(12) United States Patent
David et al.

(10) Patent No.: US 7,847,019 B2
(45) Date of Patent: Dec. 7, 2010

(54) FUNCTIONALIZED POLYMERS USING PROTECTED THIOLS

(75) Inventors: Ralph L. David, Pasadena, CA (US); Julia A. Kornfield, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 12/251,708

(22) Filed: Oct. 15, 2008

(65) Prior Publication Data

US 2009/0176941 A1 Jul. 9, 2009

Related U.S. Application Data

(60) Provisional application No. 60/998,980, filed on Oct. 15, 2007.

(51) Int. Cl.
*A61K 47/48* (2006.01)
(52) U.S. Cl. .................................. 525/54.1
(58) Field of Classification Search ............... 525/54.1
See application file for complete search history.

(56) References Cited

U.S. PATENT DOCUMENTS

| | | | |
|---|---|---|---|
| 2,947,731 | A | 8/1960 | Nummy |
| 3,705,882 | A | 12/1972 | Skillicorn |
| 3,882,156 | A | 5/1975 | Henrick et al. |
| 4,565,854 | A | 1/1986 | Sato et al. |
| 4,699,950 | A | 10/1987 | Sato et al. |
| 5,382,640 | A | 1/1995 | Emmons et al. |
| 6,977,292 | B2 | 12/2005 | Botti et al. |
| 7,301,045 | B2 | 11/2007 | Ishihara et al. |
| 2005/0014903 | A1 | 1/2005 | Kozlowski et al. |
| 2007/0021554 | A1 | 1/2007 | Urban et al. |
| 2008/0070786 | A1 | 3/2008 | Bowman et al. |

FOREIGN PATENT DOCUMENTS

| | | |
|---|---|---|
| JP | 05286894 | 11/1993 |
| WO | WO 95/00579 | 1/1995 |
| WO | WO 2004/060863 | 7/2004 |
| WO | WO 2006/069388 | 6/2006 |
| WO | WO 2007/028612 | 3/2007 |
| WO | WO 2009/052148 | 4/2009 |

OTHER PUBLICATIONS

Ameduri et al. (Jul. 1993) "Synthesis and Properties of Fluorinated Telechelic Diols Prepared by Radical Grafting of Fluorinated Thiols onto Hydroxyl-Terminated Polybutadienes," *J. Poly. Sci. A* 31(8):2069-2080.
Antonietti, M. (Web Release May 20, 1996) "Novel Amphiphilic Block Copolymers by Polymer Reactions and Their Use for Solubilization of Metal Salts and Metal Colloids," *Macromolecules* 29(11):3800-3806.
Bhatt et al. (Aug. 7, 1991) "Preparation and Thermal Properties of 4-Alkoxy-4'-cyanobiphenyl Esters of Ferrocene Dicarboxylic Acid," *J. Organomet. Chem.* 413(1-3):263-268.
Bogdal et Al. (May 31, 2002) "Synthesis and Spectral Investigation of Alkyl Methacrylates with Halogenated Carbazolyl Pendant Groups for Photonics Applications," *J. Appl. Poly. Sci.* 84(9):1650-1656.
Boutevin et al. (2000) "Synthesis and Use of Hydroxyl Telechelic Polubutadienes Grafted by 2-Mercaptoethanol for Polyurethane Resins," *J. Appl. Poly. Sci.* 75(13):1655-1666.
Brace, N. O. (Sep. 1966) "Cyclization Reactions of Perfluoroalkyl-Substituted Radicals," *J. Org. Chem.* 31(9):2879-2885.
Carlise et al. (Jun. 15, 2004) "Side-Chain Functionalized Polymers Containing Bipyridine Coordination Sites: Polymerization and Metal-Coordination Studies," *J. Poly. Sci. A Poly. Chem.* 42(12):2973-2984.
Chung et al. (Jul. 1988) "Synthesis of Functional Hydrocarbon Polymers with Well-Defined Molecular Structures," *Macromolecules* 21(7):1903-1907.
Cramer et al. (Web Release May 31, 2002) "Photopolymerizations of Thiol-Ene Polymers without Photoinitiators," *Macromolecules* 35(14):5361-5365.
David et al. (Jan. 25, 2008) "Facile, Efficient Routes to Diverse Protected Thiols and to Their Deprotection and Addition to Create Functional Polymers by Thiol-Ene Coupling," *Macromolecules* 41(4):1151-1161.
David, R.L. A. (Defense Date Mar. 7, 2008) "Associative Polymers as Antimisting Agents and Other Functional Materials via Thiol-Ene Coupling," Ph.D. Thesis, California Institute of Technology, Pasadena, CA, Abstract Only.
Fabris et al. (Web Release Dec. 14, 2005) "Gold Nanoclusters Protected by Conformationally Constrained Peptides," *J. Am. Chem. Soc.* 128(1):326-336.
Förster, S. (Feb. 1998) "Amphiphilic Block Copolymers in Structure-Controlled Nanomaterial Hybrids," *Adv. Mater.* 10(3):195-217.
Geng et al. (Web Release Oct. 20, 2006) "Grafting Short Peptides onto Polybutadiene-*block*-poly(ethylene oxide): A Platform for Self-Assembling Hybrid Amphiphiles," *Angew. Chem. Int. Ed.* 45(45):7578-7581.
Guo et al. (Nov. 1990) "Catalytic Hydrosilylation of Diene-Based Polymers. 1. Hydrosilylation of Polybutadiene," *Macromolecules* 23(24):5047-5054.

(Continued)

*Primary Examiner*—Ling-Siu Choi
*Assistant Examiner*—Sonya Wright
(74) *Attorney, Agent, or Firm*—Greenlee Sullivan P.C.

(57) ABSTRACT

A process for the preparation of functional molecules using the thiol-ene coupling reaction and a process for the preparation of protected functional thiols, specifically thioesters is provided. The methods may be used to make functional polymers and other molecules. The method of making a functionalized polymer using a thiol-ene reaction comprises: providing a functionalized thioester having the following formula:

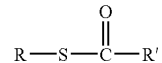

wherein R is a functional group and COR' is a protecting group; cleaving the functionalized thioester, forming a functional thiol and an acyl group; providing a polymer having a pendant vinyl group; and reacting the polymer with the functional thiol whereby a functionalized polymer is formed, wherein the functional thiol is not isolated prior to reacting with the polymer.

7 Claims, 11 Drawing Sheets

OTHER PUBLICATIONS

Hinou et al. (2003) "Systematic Synthesis and Inhibitory Activities of Bisubstrate—Type Inhibitors of Sialyltransferase," *J. Org. Chem.* 68(14):5602-5613.

Hordyjewicz-Baran et al. (Web Release Apr. 26, 2007) "Bioinspired Polymer Vesicles Based on Hydrophilically Modified Polybutadienes," *Macromolecules* 40(11):3901-3903.

International Search Report and Written Opinion, Corresponding to International Application No. PCT/US08/79945, Mailed Dec. 24, 2008.

Justynska et al. (2005) "Toward a Toolbox of Functional Block Copolymers via Free-Radical Addition of Mercaptans, " *Polymer* 46(26):12057-12064.

Justynska et al. (Jul. 2006) "New Functional Diblock Copolymers Through Radical Addition of Mercaptans," *Macromolecular Symposia* 240:41-46.

Kempe, M.D. (2004) "Rheology and Dynamics of Side-Group Liquid Crystalline Polymers in Nematic Solvents," Ph.D. Thesis, California Institute of Technology, Pasadena, CA, Abstract Only.

Kimyonok et al. (Jan. 23, 2007) "Poly(cyclooctenes)s with Pendant Fluorescent and Phosphorescent Metal Complexes," *Macromol. Rapid Commun.* 28(2):152-157.

Kocienski, P.J. (2004) "Thiol Protecting Groups," In; *Protecting Groups*, $3^{rd}$ ed., Thieme: Ch.5, pp. 365-391.

Krämer et al. (Web Release Mar. 24, 1998) "Synthesis of Nanoporous Silica with New Pore Morphologies by Templating the Assemblies of Ionic Block Copolymers," *Langmuir* 14(8):2027-2031.

Kukula et al. (Web Release Feb. 20, 2002) "The Formation of Polymer Vesicles or 'Peptosomes' by Polybutadiene-*block*-poly(L-glutamate)s in Dilute Aqueous Solution," *J. Am. Chem. Soc.* 124(8):1658-1663.

Masamune et al. (1975) "A General, Selective Synthesis of Thiol Esters," *Can. J. Chem.* 53: 3693-3695.

Meyers et al. (Web Release Feb. 19, 2003) "Design and Synthesis of $Alq_3$-Functionalized Polymers," *Macromolecules* 36(6):1766-1768.

Moreau et al. (Web Release Nov. 15, 2003) "Approaches Towards the Total Synthesis of the Nine-Membered Thio-Lactone Core of Griseoviridin," *J. Org. Chem.* 68(25):9874.

Moreau et al. (Web Release Jun. 6, 2003) "Approaches Towards the Total Synthesis of the Nine-Membered Thio-Lactone Core of Griseoviridin," *J. Org. Chem.*68(13):5346-5350.

Morii et al. (Web Release Jun. 27, 2005) "Synthetic Studies on Oligosaccharides Composed of 5-Thioglucopyranose Units," *Bioorg. Med. Chem.* 13(17):5113-5144.

Nakatsuji et al. (Web Release Feb. 1, 2003) "Novel Radical Compounds Bearing Mesogenic Corers with Long Alkyl Substituents," *J. Org. Chem.* 68(5):1708-1714.

Narayan et al. (Web Release May 20, 2005) "Versatile and Stereoselective Synthesis of Orthogonally Protected β-Methylcysteine and β-Methyllanthionine," *Org. Lett.* 7(13):2655-2658.

Neises et al. (1978) "Simple Method for the Esterification of Carboxylic Acids,"*Angew. Chem. Int. Ed. Engle.* 17(7):522-524.

Olia et al. (Feb. 7, 2005) "Synthesis of a Novel Carboxy Functionalized PyOX-Ligand," *Tetrahedron Lett.* 46(6):967-969.

Pittelkow et al. (2004) "TFFH as an Excellent Reagent for Acylation of Alcohols, Thiols and Dithio-Carbamates," *Synthesis* 15:2485-2492.

Pollino et al. (Web Release Dec. 10, 2003) "One-Step Multifunctionalization of Random Copolymers via Self-Assembly," *J. Am. Chem. Soc.* 126(2):563-567.

Ramakrishnan, S. (Jun. 1991) "Well-Defined Ethylene-Vinyl Alcohol Copolymers via Hydroboration: Control of Composition and Distribution of the Hydroxyl Groups on the Polymer Backbone," *Macromolecules* 24(13):3753-3759.

Ren et al. (Web Release Jun. 9, 2001) "A Simple Mild Route to Highly Fluorinated Model Polymers," *Macromolecules* 34(14):4780-4787.

Rich et al. (2006) "Chemical and Chemoenzymatic Synthesis of S-Linked Ganglioside Analogues and their Protein Conjugates for Use as Immunogens," *Chemistry A European J.* 12(3):845-858.

Schapman et al. (1998) "Low Molar Mass Polybutadiene Made Crosslinkable by Silane Moities Introduced Via Addition of Thiol to Double Bond: 3. Synthesis and Kinetic Study," *Polymer* 39(20):4955-4962.

Schultz et al. (1982) "Revent Advances in the Chemical Modification of Unsaturated Polymers," *Rubber Chem. Technol.* 55(3):809-859.

Scruggs, N.R. (2007) "Coupling Polymer Thermodynamics and Viscoelasticity to Liquid Crystalline Order: Self Assembly and Relaxation Dynamics of Block Copolymers in a Nematic Solvent," Ph.D Thesis, California Institute of Technology, Pasadena, CA.

South et al. (Web Release Oct. 26, 2006) "Modular and Dynamic Functionalization of Polymeric Scaffolds," *Acc. Chem. Res.* 40(1):63-74.

Verduzco, R. (Defense Date Feb. 5, 2007) "Self-Assembled Liquid Crystal Polymer Gels," Ph.D Thesis, California Institute of Technology, Pasadena, CA, Abstract Only.

Wardell, J.L. (1974) "Preparation of Thiols," In; Patao. S. ed. *The Chemistry of the Thiol Group*, Part 1, Wiley; Ch. 4, pp. 163-269.

Wuts et al. (2007) Protection for the Thiol Group; In; *Greene's Protective Groups in Organic Synthesis*, Peter et al. Eds., John Wiley and Sons, Inc., Ch. 6, pp. 647-695.

Yamaaguchi et al. (Web Release Nov. 3, 2006) "Self-Assembly of Amphiphilic Liquid Crystalline Oligomers Possessing a Semiperfluorinated Alkyl Chain," *Chem. Mater.* 18(24):5704-5710.

FUNCTIONALIZED POLYMERS USING PROTECTED THIOLS

CROSS-REFERENCE TO RELATED APPLICATIONS

This application takes priority from U.S. provisional application Ser. No. 60/998,980, filed Oct. 15, 2007, the disclosure of which is hereby incorporated by reference to the extent not inconsistent with the disclosure herein.

STATEMENT ON FEDERALLY SPONSORED RESEARCH OR DEVELOPMENT

Not applicable.

BACKGROUND OF THE INVENTION

This invention relates to functional polymers and functional protected thiol compounds, methods of preparation and use.

Functionalization of polymers having pendant vinyl groups using thiol-ene coupling is a powerful and versatile method to prepare well-defined polymeric materials with tailored properties. However, commercially available mercaptans are limited to a select few functional groups. Methods of preparing polymers having a variety of functional groups are needed.

SUMMARY OF THE INVENTION

According to the present invention there is provided a process for the preparation of functional polymers and other molecules using the thiol-ene coupling reaction and a process for the preparation of protected functional thiols, specifically thioesters.

Generally the method of making functional polymers comprises reacting a protected functional thioester with a deprotecting agent and a polymer having one or more pendant vinyl groups.

The protected functional thioesters prepared using the methods of the invention can be stored and used when desired by deprotecting and reacting with a desired molecule such as a polymer having one or more pendant vinyl groups.

More specifically, provided is a method of making a functionalized polymer using a thiol-ene reaction comprising: providing a functionalized thioester having the following formula:

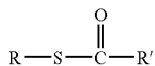

wherein R is a functional group and COR' is a protecting group; cleaving the functionalized thioester, forming a functional thiol and an acyl group; providing a polymer having a pendant vinyl group; and reacting the polymer with the functional thiol whereby a functionalized polymer is formed, wherein the functional thiol is not isolated prior to reacting with the polymer. In an embodiment, the cleaving step is performed by reacting the functionalized thioester with a cleaving agent. In an embodiment, the cleaving agent is hydrazine. In an embodiment, the hydrazine is a hydrazine salt or solution thereof. In an embodiment, the hydrazine salt is hydrazine acetate. In an embodiment, the hydrazine acetate is formed from reaction of hydrazine HCl with NaOAc in DMF. In an embodiment, the protecting group is an acetyl or benzoyl group. The protected functional thioester is deprotected insitu in the reaction and is not isolated as a separate thiol molecule. In an embodiment, the method of making a functionalized polymer is a one-pot reaction.

The methods of the invention can be used to functionalize other molecules having one or more vinyl groups by one of ordinary skill in the art without undue experimentation. The methods of the invention can be used to add a functional group to a molecule having a single vinyl group available for reaction, for example. For example, in molecular synthesis of fine chemicals and drugs a C—S bond is often desired. The methods described here can be used to conveniently add a functional group in a synthetic pathway.

The polymer having a pendant vinyl group is a polymer having one or more vinyl groups available for reaction. In an embodiment, the polymer is a polybutadiene. In an embodiment, the polymer comprises a 1,2 polybutadiene unit. In an embodiment, the polymer comprises a polymer or copolymer of butadiene having 1,2-polybutadiene units. As known in the art, polybutadienes may be prepared with a wide distribution of molecular weight and density of double bonds. The use of all such distributions and densities are intended to be included herein. The number of pendant vinyl groups and the extent of reaction as determined by reaction conditions (specifically the concentration of reactants and the reaction time) determine the final structure obtained after reaction. These variables are well known in the art. Other useful polymers include any polymer or copolymer of butadiene, isoprene, 2-n-heptyl-1,3-butadiene, ethylene, isobutylene, 1-butene, acrylonitrile, methacrylonitrile, crotonitrile, vinyl acetate, vinyl benzoate, vinyl methyl ether, vinyl n-butyl ether, allyl propionate, allyl benzoate, allyl methyl ester or 5-vinyl-2-norbornene. In embodiments, useful polymers include: polymers and copolymers of styrene, vinyl benzyl chloride (hereinafter (VBC)), VBC/styrene/divinylbenzene (hereinafter DVB), butadiene/styrene/VBC, VBC/butadiene/acrylonitrile, acrylonitrile/styrene/VBC and isoprene/VBC. The identified polymers are not intended to be an exhaustive list of useful polymers. This disclosure is intended to include other polymers that have a pendant vinyl group. These polymers are known to one of ordinary skill in the art.

The polymer having a pendant vinyl group and the functionalized thioester are combined in the desired stoichiometric ratio to allow the desired amount of functionalization of the polymer to occur. In one embodiment of the invention, the amount of pendant vinyl group:functionalized thioester ranges from 0.1 to 100 mol/mol ratio. In one embodiment of the invention, the amount of pendant vinyl group:functionalized thioester ranges from 0.01 to 100 mol/mol ratio. In one embodiment of the invention, the amount of pendant vinyl group:functionalized thioester ranges from 0.5-1.5 mol/mol ratio. The stoichiometric amount is selected based on the desired C═C/SH molar ratio.

In an embodiment, the reactions described here are carried out at a suitable temperature as easily determined by one of ordinary skill in the art without undue experimentation. In an embodiment, a reaction is carried out at a temperature selected over the range of 10 degrees Celsius to 150 degrees Celsius. In embodiments, useful solvents for the methods described herein include: a dimethoxyethane solvent, an ether, a halogenated solvent, or an aromatic solvent. In embodiments, useful solvents for the methods described herein include dimethoxyethane, tetrahydrofuran, chloroform, toluene, benzene, ethylbenzene, xylenes, tetrachloroethane, methanol:THF, or methanol:chloroform. In embodiments, the solvent is 20:80 methanol:THF. In embodiments, the solvent is 20:80 methanol:chloroform. As known in the art, mixtures of solvents may be used. Such mixtures are included in the disclosure herein, and are easily determined by one of ordinary skill in the art without undue experimentation.

In an embodiment, the functional group is selected from the group consisting of: amino acid, peptide, polypeptide, nucleic acid, lipid, carbohydrate, carbazole, benzoate, phenol, pyridine, cyanobiphenyl, perfluorocarbon, polyethylene oxide (PEO) and polypropyleneoxide (PPO) groups. In embodiments, small (i.e. MW 500 to 5000) polyethylene oxide (PEO) or polypropyleneoxide (PPO) groups are used. The functional groups specifically identified herein are not intended to be limiting. This disclosure is intended to include other desired functional groups that can be used in the methods of the invention without undue experimentation.

In an embodiment, the reaction of the polymer with the functional thiol is initiated by a free-radical initiator. Any suitable initiator/method of initiation may be used, including thermal activation and light activation (such as using UV light). When light, particularly UV light, is used for the reaction, a photoinitiator may be required, as known in the art. Initiators and their use are known in the art. In embodiments, the initiator is chosen from 2,2-azobisisobutyronitrile (AIBN), benzoyl peroxide (BPO), diisopropyl peroxydicarbonate (IPP), t-butylhydroperoxide (TBPO), heat-activated initiators, and light-activated initiators such as camphorquinone (Aldrich), 4-(2-hydroxyethoxy)-phenyl-(2-hydroxy-2-methylpropyl)ketone (Irgacure 2959, Ciba-Geigy) and mixtures thereof. The amount of initiator used is well known in the art, is chosen for a given reaction temperature to achieve a target rate of initiation, and is typically 0.1% to 20% molar equivalent of the reactants involved in the radical reactions.

Also provided in an embodiment is a method of preparing a functionalized thioester comprising: (a) reacting a starting material having a desired functional group with a nonsymmetrical bifunctional linker molecule, forming a functionalized intermediate and (b) reacting the functionalized intermediate with a thiol acid to form a functionalized thioester. As used herein, "functionalized thioester" is intended to be a protected thiol. In an embodiment, the starting material is a nucleophile. In an embodiment, the starting material is an electrophile.

In embodiments, the method of preparing a functionalized thioester can take a variety of forms. Although Applicant does not wish to be bound by theory, the following nonlimiting examples are provided. In one embodiment, a nucleophilic substitution reaction of a nucleophile having a desired functional group with a nonsymmetrical bifunctional linker molecule having two leaving groups (such as ClCH$_2$CH$_2$OTs) is followed by reaction with a thiol acid to form the functionalized thioester (i.e., a protected thiol). "Ts" stands for the tosyl group. In one embodiment, a nucleophilic substitution reaction of a nucleophile having a desired functional group with a nonsymmetrical bifunctional linker molecule having one leaving group (such as a chloroalcohol, for example H(OCH$_2$CH$_2$)$_n$Cl, where n is an integer from 1 to 10, for example) is followed by conversion of the linker's other functional group into a leaving group (e.g. in the example of a chloroalcohol as the linker, conversion of the hydroxyl group into a tosylate or other leaving group), followed by reaction with a thiol acid to form the functionalized thioester. This reaction allows the use of harsher conditions for the first step, and is a convenient way to incorporate linkers of different lengths. In one embodiment, esterifying a carboxylic acid nucleophilic starting material with a chloroalcohol nonsymmetrical bifunctional linker molecule, followed by reaction with a thiol acid is used to form the functionalized thioester. In one embodiment, reacting a nucleophilic starting material having a desired functional group with allyl bromide followed by a radical reaction with a thioacid is used to form the functionalized thioester.

As used herein, a "nonsymmetrical bifunctional linker molecule" contains two different functional groups: one functional group binds to the starting material functional group and the other functional group binds to a thiol group. As used herein, "binds" generally indicates covalent bonding between two moieties.

The thiol acid (also referred to as thioacid) used can be any thiol acid. In embodiments, the thiol acid is thiobenzoic acid or thioacetic acid. In embodiments, the nucleophilic starting material is a carboxylic acid, an alcohol, an amine, a phenol, or a heterocyclic nitrogen compound. In embodiments, the bifunctional linker molecule is a chloroalcohol or allylbromide. In embodiments, the bifunctional linker molecule is a Cl CH$_2$CH$_2$OTs or H(OCH$_2$CH$_2$)$_n$Cl, where n is an integer from 1 to 10, for example. In embodiments, the bifunctional linker molecule is any molecule which is capable of linking a nucleophilic starting material with a thioacid.

In an embodiment, the protecting group for the thiol moiety is an acetyl or benzoyl group. The protecting groups listed specifically are not intended to be limiting, and other suitable protecting groups may be used.

In embodiments, the functional group is selected from those functional groups described above. In embodiments, the solvent for the first step in the reactions is DMSO, although other solvents may be used, as known in the art including those suitable solvents and solvent mixtures described elsewhere herein.

Also provided is a functionalized thioester made by the methods described herein. Also provided is a functionalized polymeric material made by the methods described herein.

Also provided is a functionalized thioester having the following formula:

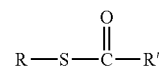

wherein R is a functional group and COR' is a protecting group that is readily cleaved to provide a functional thiol that may be used without isolation to perform thiol-ene coupling. The functional groups and protecting groups can be selected from those groups described herein.

Also provided is a method of making a functionalized molecule using a thiol-ene reaction comprising:

providing a functionalized thioester having the following formula:

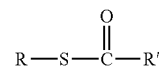

wherein R is a functional group and COR' is a protecting group; cleaving the functionalized thioester, forming a functional thiol and an acyl group; providing a molecule having a pendant vinyl group; reacting the molecule with the functional thiol whereby a functionalized molecule is formed, wherein the functional thiol is not isolated prior to reacting with the molecule. The molecule can be any molecule having a pendant vinyl group, including small molecules and fine chemicals.

All reactions are carried out under suitable reaction conditions as known in the art. Suitable reaction conditions include temperature, time, solvent(s) and other aspects of organic synthesis that one of ordinary skill in the art is easily able to determine without undue experimentation using the description provided herein and the knowledge of one of ordinary skill in the art. For example, the thiol-ene radical reaction temperature is any suitable temperature, such as between 10° to 150° C., depending on the type of initiator used.

It will be appreciated that the groups specifically identified in the protected functionalized thioester moiety may be connected to each other with a suitable linker or other group, as known in the art. For example, the functional group may be connected to the thioester group with one or more atoms or groups. Also the carbon of the thioester group may be connected to the protecting group with one or more atoms or groups, for example methylene linkers. For example, optionally substituted alkyl, benzyl, or aryl groups can be used including linear or branched alkyl groups, cyclic aromatic or non-aromatic, heterocyclic aromatic or non-aromatic structures, all of which may be optionally substituted with one or more of the same or different substituents. The optional substituents include one or more of electron donating or electron donating groups, such as heteroatoms in the chain or attached to the chain, carbonyl, nitrile, sulfoxy, sulfone, sulfate, halogen, C1-C6 linear or branched alkyl groups, benzyl, benzyl groups, ketone, ester, amino, nitro, I, Br, Cl, F, and other groups which are known in the art.

DETAILED DESCRIPTION OF THE INVENTION

Figure 1:
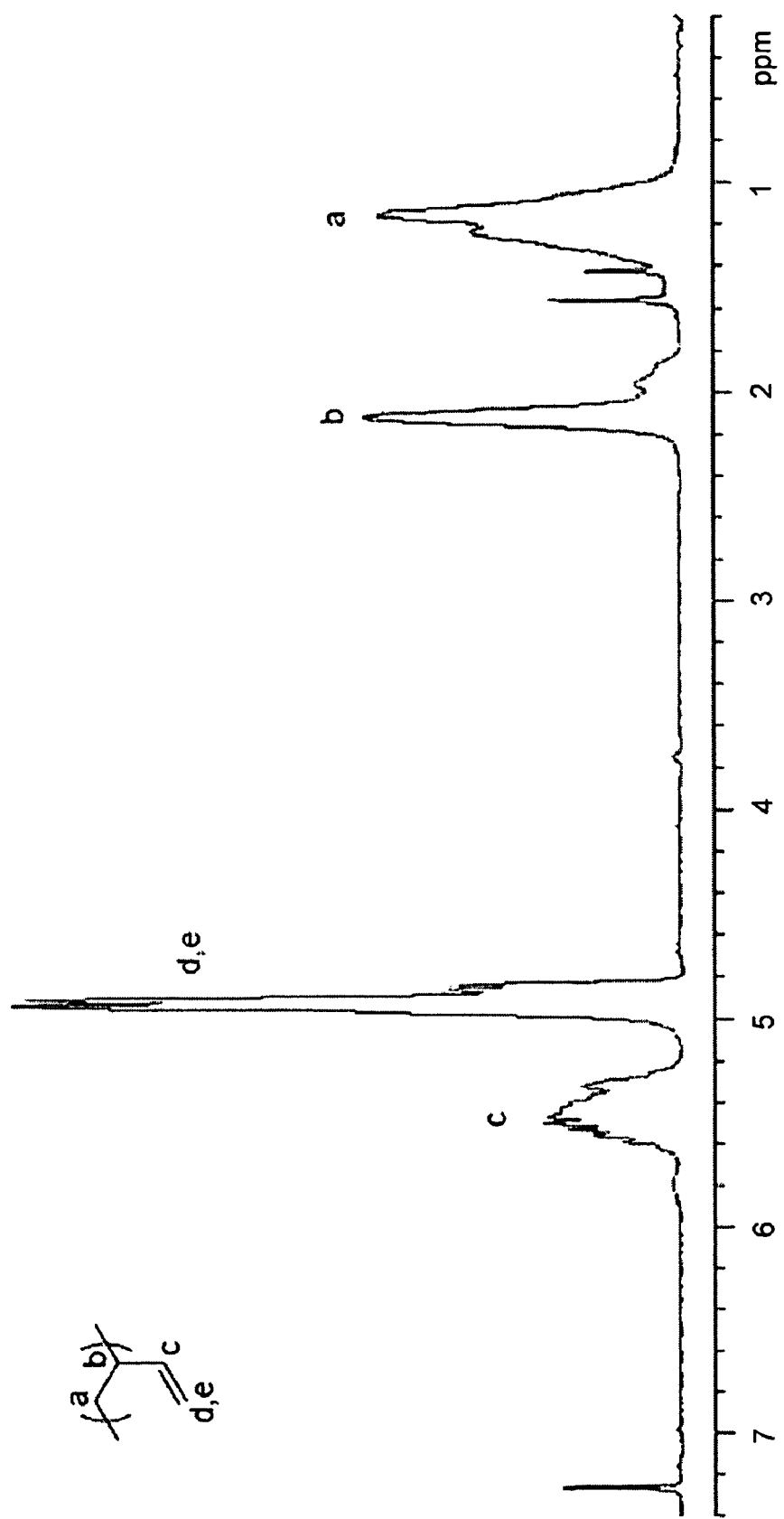
FIG. 1 is a $^1$H NMR trace of unfunctionalized polymer 92 kg/mol 1,2-PB.
Figure 2:
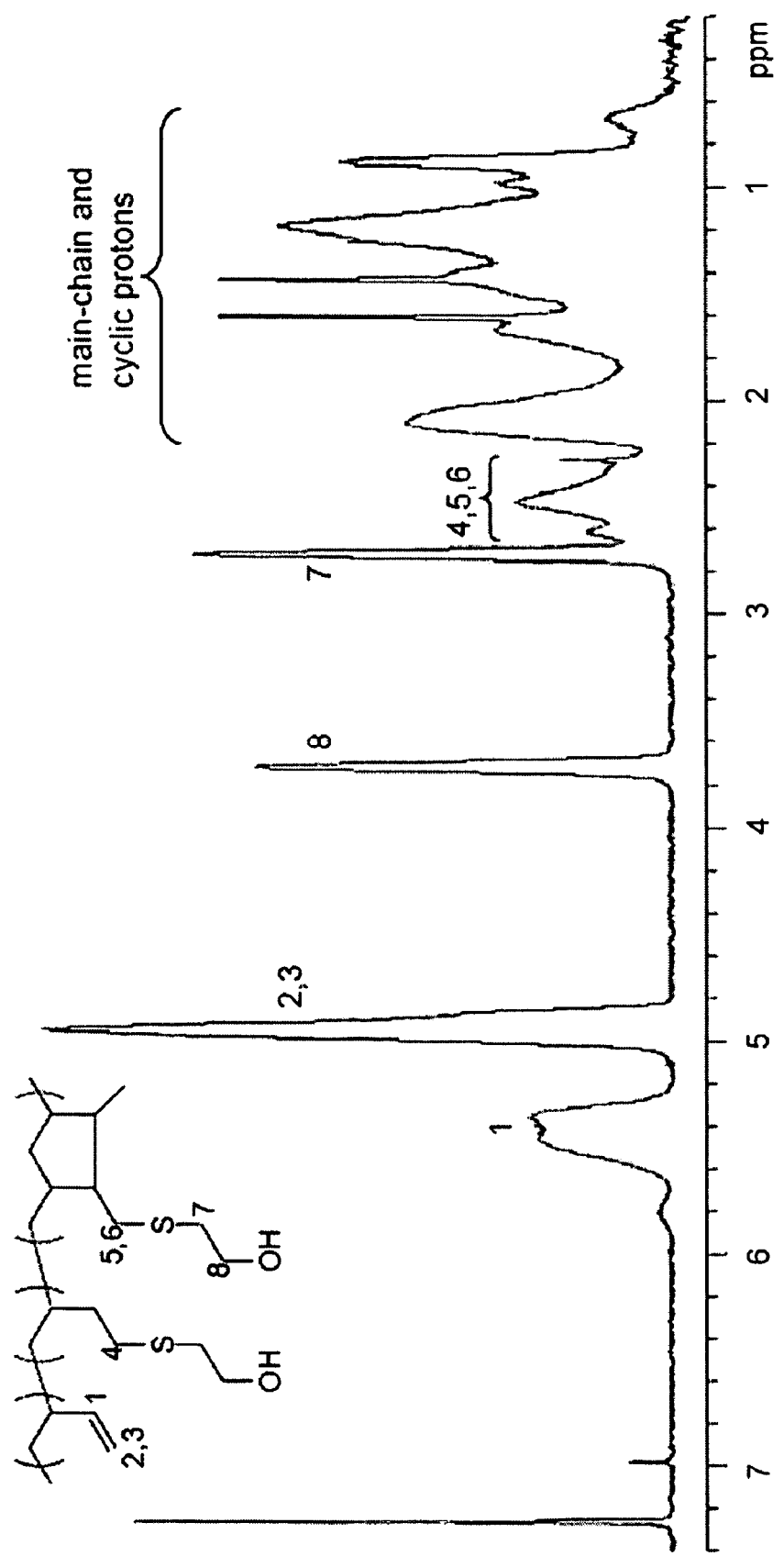
FIG. 2 is a $^1$H NMR trace of functionalized 1,2-PB polymer 92kPB-OH (experimental conditions are given in Table 2).
Figure 3:
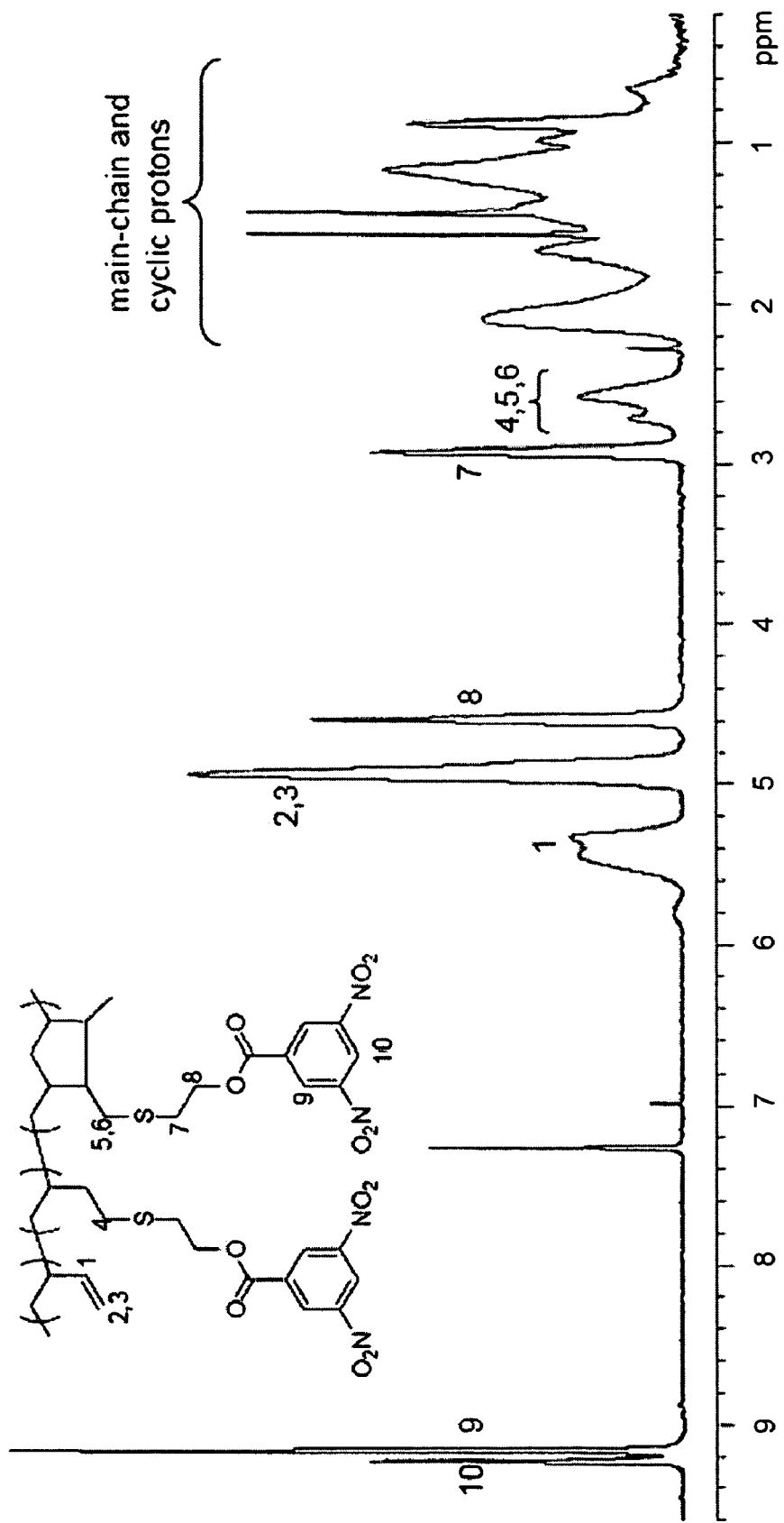
FIG. 3 is a $^1$H NMR trace of functionalized 1,2 PB polymer 92kPB-DNB (experimental conditions are given in Table 2).
Figure 4:
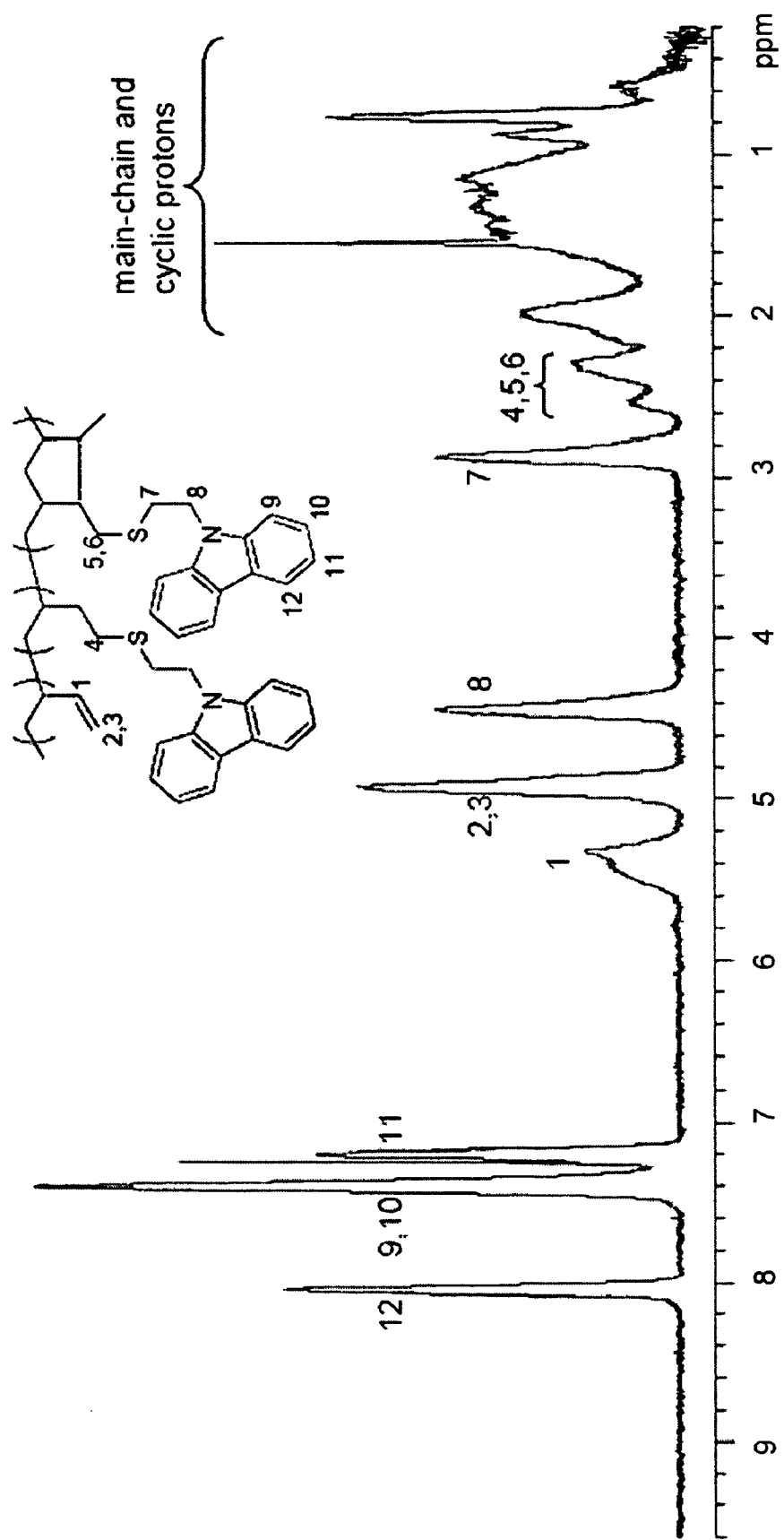
FIG. 4 is a $^1$H NMR trace of functionalized 1,2 PB polymer 820kPB8 (experimental conditions are given in Table 1).
Figure 5:
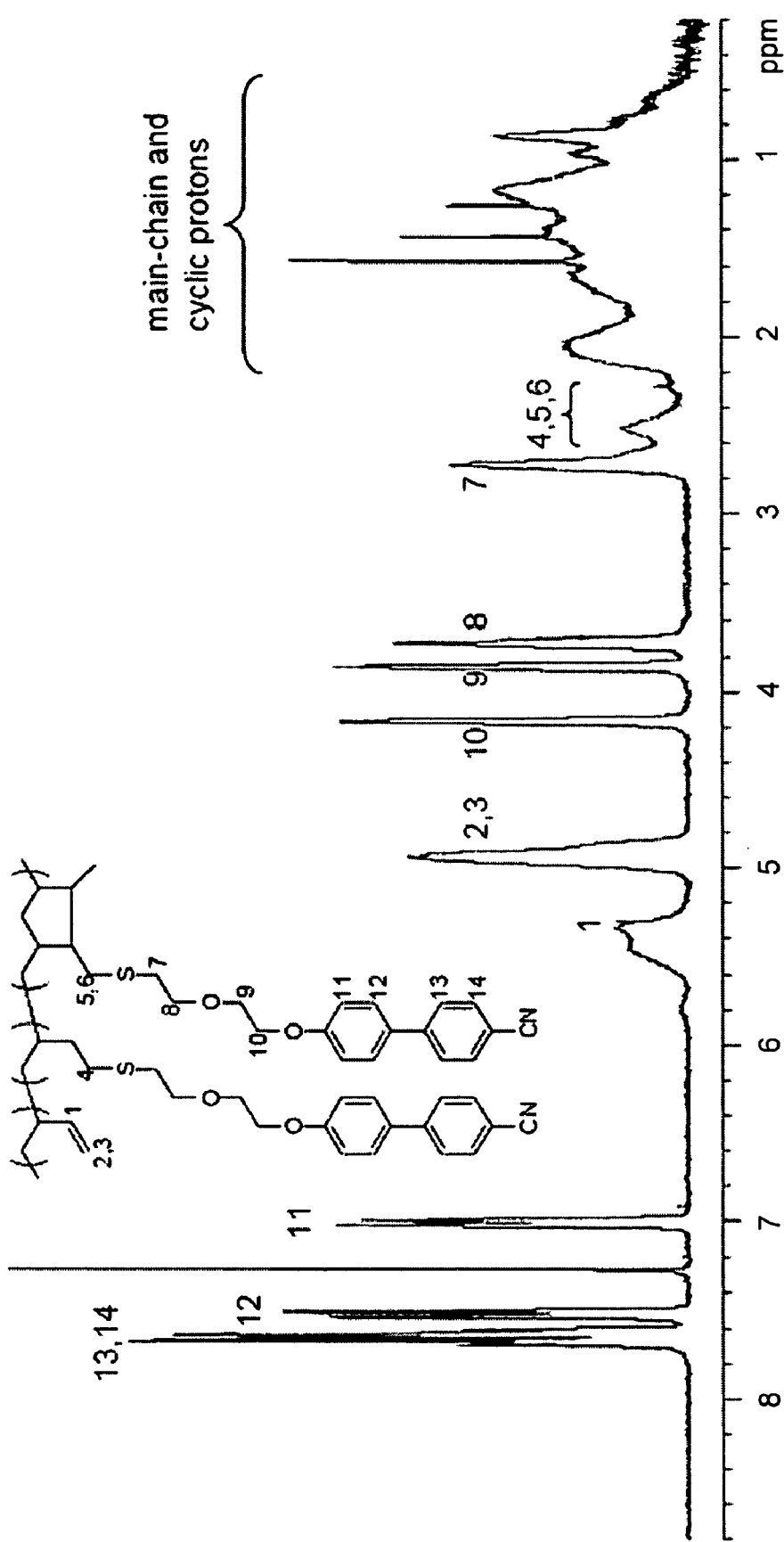
FIG. 5 is a $^1$H NMR trace of functionalized 1,2 PB polymer 92kPB6 (experimental conditions are given in Table 1).
Figure 6:
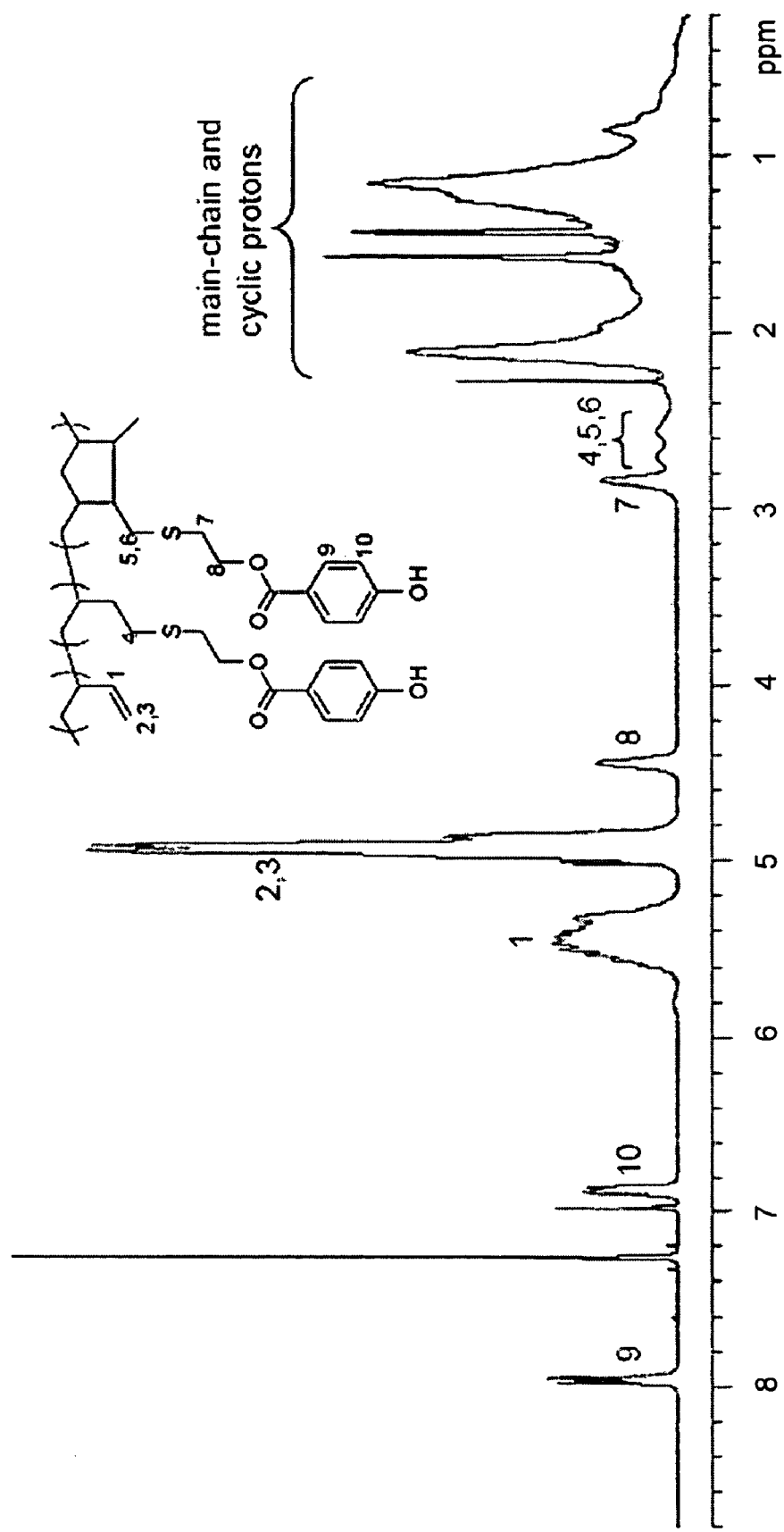
FIG. 6 is a $^1$H NMR trace of functionalized 1,2 PB polymer 820kPB12 (experimental conditions are given in Table 1).

Unless defined otherwise, all technical and scientific terms used herein have the broadest meanings as commonly understood by one of ordinary skill in the art to which this invention pertains. In addition, herein, the following definitions apply:

Alkyl groups include straight-chain, branched and cyclic alkyl groups. Alkyl groups include those having from 1 to 30 carbon atoms. Alkyl groups include small alkyl groups having 1 to 3 carbon atoms. Alkyl groups include medium length alkyl groups having from 4-10 carbon atoms. Alkyl groups include long alkyl groups having more than 10 carbon atoms, particularly those having 10-30 carbon atoms. Cyclic alkyl groups include those having one or more rings. Cyclic alkyl groups include those having a 3-, 4-, 5-, 6-, 7-, 8-, 9- or 10-member carbon ring and particularly those having a 3-, 4-, 5-, 6-, or 7-member ring. The carbon rings in cyclic alkyl groups can also carry alkyl groups. Cyclic alkyl groups can include bicyclic and tricyclic alkyl groups. Alkyl groups are optionally substituted. Substituted alkyl groups include among others those which are substituted with aryl groups, which in turn can be optionally substituted. Specific alkyl groups include methyl, ethyl, n-propyl, iso-propyl, cyclopropyl, n-butyl, s-butyl, t-butyl, cyclobutyl, n-pentyl, branched-pentyl, cyclopentyl, n-hexyl, branched hexyl, and cyclohexyl groups, all of which are optionally substituted. Substituted alkyl groups include fully halogenated or semihalogenated alkyl groups, such as alkyl groups having one or more hydrogens replaced with one or more fluorine atoms, chlorine atoms, bromine atoms and/or iodine atoms. Substituted alkyl groups include fully fluorinated or semifluorinated alkyl groups, such as alkyl groups having one or more hydrogens replaced with one or more fluorine atoms. An alkoxyl group is an alkyl group linked to oxygen and can be represented by the formula R—O.

Alkenyl groups include straight-chain, branched and cyclic alkenyl groups. Alkenyl groups include those having 1, 2 or more double bonds and those in which two or more of the double bonds are conjugated double bonds. Alkenyl groups include those having from 2 to 20 carbon atoms. Alkenyl groups include small alkenyl groups having 2 to 3 carbon atoms. Alkenyl groups include medium length alkenyl groups having from 4-10 carbon atoms. Alkenyl groups include long alkenyl groups having more than 10 carbon atoms, particularly those having 10-20 carbon atoms. Cyclic alkenyl groups include those having one or more rings. Cyclic alkenyl groups include those in which a double bond is in the ring or in an alkenyl group attached to a ring. Cyclic alkenyl groups include those having a 3-, 4-, 5-, 6-, 7-, 8-, 9- or 10-member carbon ring and particularly those having a 3-, 4-, 5-, 6- or 7-member ring. The carbon rings in cyclic alkenyl groups can also carry alkyl groups. Cyclic alkenyl groups can include bicyclic and tricyclic alkyl groups. Alkenyl groups are optionally substituted. Substituted alkenyl groups include among others those which are substituted with alkyl or aryl groups, which groups in turn can be optionally substituted. Specific alkenyl groups include ethenyl, prop-1-enyl, prop-2-enyl, cycloprop-1-enyl, but-1-enyl, but-2-enyl, cyclobut-1-enyl, cyclobut-2-enyl, pent-1-enyl, pent-2-enyl, branched pentenyl, cyclopent-1-enyl, hex-1-enyl, branched hexenyl, cyclohexenyl, all of which are optionally substituted. Substituted alkenyl groups include fully halogenated or semihalogenated alkenyl groups, such as alkenyl groups having one or more hydrogens replaced with one or more fluorine atoms, chlorine atoms, bromine atoms and/or iodine atoms. Substituted alkenyl groups include fully fluorinated or semifluorinated alkenyl groups, such as alkenyl groups having one or more hydrogens replaced with one or more fluorine atoms.

Aryl groups include groups having one or more 5- or 6-member aromatic or heteroaromatic rings. Aryl groups can contain one or more fused aromatic rings. Heteroaromatic rings can include one or more N, O, or S atoms in the ring. Heteroaromatic rings can include those with one, two or three N, those with one or two O, and those with one or two S, or combinations of one or two or three N, O or S. Aryl groups are optionally substituted. Substituted aryl groups include among others those which are substituted with alkyl or alkenyl groups, which groups in turn can be optionally substituted. Specific aryl groups include phenyl groups, biphenyl groups, pyridinyl groups, and naphthyl groups, all of which are optionally substituted. Substituted aryl groups include fully halogenated or semihalogenated aryl groups, such as aryl groups having one or more hydrogens replaced with one or more fluorine atoms, chlorine atoms, bromine atoms and/or iodine atoms. Substituted aryl groups include fully fluorinated or semifluorinated aryl groups, such as aryl groups having one or more hydrogens replaced with one or more fluorine atoms.

Polymers are molecules or nanoparticles comprising multiple repeating units, including but not limited to synthetic homopolymers, copolymers and block copolymers; oligopeptides, polypeptides and proteins; oligonucleotides and polynucleotides; oligosaccharides and polysaccharides; hyperbranched molecules and dendrimers; latex particles and organic/inorganic particles and inorganic particles bearing organic functional groups on their surfaces. It is understood that the methods of the invention may be applied to cross linked polymers and to polymers attached to surfaces or in pores. When applied to immobilized polymers, it is understood that the methods of the invention can be applied in a spatially resolved manner by using spatially-resolved generation of radicals.

The invention will now be illustrated by way of example only and with reference to the following non-limiting examples and experiments.

There are several known protecting groups for thiols that can be used in the present invention. For example, see Wuts, P. G. M., Greene's Protective Groups in Organic Synthesis/Peter G. M. Wuts and Theodora W. Greene. 4th ed.; Wiley-Interscience: 2007; ch 6; and Kocienski, P. J., Protecting Groups. 3rd ed.; Thieme: 2004; ch 5.

The methods described here can be used for grafting various functionalities in a one-step polymer reaction (as opposed to hydroboration or epoxidation). Thiol-ene coupling described here proceeds under mild reaction conditions and is tolerant of a large number of functional groups. In particular, the chemistry is water insensitive, which renders it considerably simpler than hydrosilylation, for instance. The thiol addition described here also proceeds with minimal cross-linking or chain scission in comparison to other modification reactions such as hydroboration/oxidation[13] and hydrosilylation[23,24]. Finally, desired side-groups are incorporated via unobtrusive thioether linkages, without the introduction of additional functionalities (in contrast to functionalization by epoxidation or radical addition of alkyl iodides, which add one molar equivalent of hydroxyl, chloro, or iodo functionalities per grafted side group).

Thiol-ene addition to PB and other polymers having pendant vinyl groups offers tremendous versatility for molecular design. The excellent tolerance of thiol-ene coupling to numerous functional groups combines with the good availability of polymers of well-defined microstructures (e.g., content of 1,2-adducts in PB), macromolecular structure (such as chain topology and incorporation of other polymer blocks), and size (from $<10^4$ g/mol to $>10^6$ g/mol). If desired, a polymer having pendant vinyl groups can be synthesized according to known methods. The method is well suited to produce a homologous series of model materials (i.e., having precisely matched degree of polymerization, but varying in functionality and/or in extents of functionalization) that elucidate macromolecular physical phenomena.

The main drawback to currently available thiol-ene reactions is the limited range of commercially available mercaptans (essentially limited to carboxylic acid, alcohol, 1,2-diol, amine, alkyl, and fluoroalkyl functionalities). Therefore, the rapid, high-yield synthetic methods to prepare desired functional thiols described herein are needed to make thiol-ene functionalization widely useful. Furthermore, technological application requires that these synthetic methods be amenable to scale up. Indirect preparation of thiols through thioester intermediates as described herein presents significant advantages with regard to safety, yield, and product stability. Facile procedures to deprotect the thiols and—without isolation—proceed to functionalize 1,2-PB are described (e.g., Scheme 1). Thus, this invention shows how to conveniently extend the number of candidate side-groups for functionalization of polymers by thiol-ene coupling.

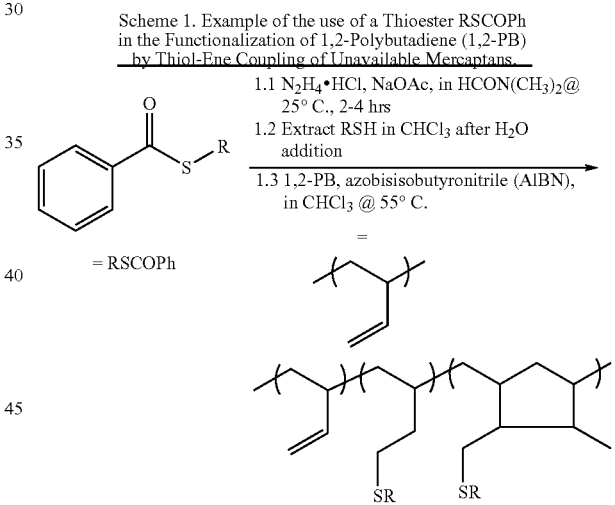

Scheme 1. Example of the use of a Thioester RSCOPh in the Functionalization of 1,2-Polybutadiene (1,2-PB) by Thiol-Ene Coupling of Unavailable Mercaptans.

Exemplified herein are highly efficient synthetic routes to an array of protected thiols which were chosen both i) because the featured side-groups are important functionalities in their own right, and ii) because each is representative of a general pathway for incorporation of the thiol moiety (e.g., Scheme 2). Specifically, phenol and pyridine functionalities are described because of their relevance as hydrogen-bond donor and acceptor; carbazole and dinitrobenzoate are of interest as electron donor and acceptor, and relevant to materials with novel electronic properties; and 4-cyano-4'-hydroxybiphenyl is of interest for its liquid-crystalline properties. Of paramount practical significance, the described chemistry involves: i) inexpensive, readily available reagents of moderate toxicity and reactivity, ii) no elaborate equipment or procedures, iii) rapid, quantitative conversions of limiting reagents in all steps without measurable formation of side-products, and iv) simple purification (enabled by the clean synthetic routes) using scalable separation processes (principally liquid-liquid extraction and washes, occasionally recrystallization, but no column separations).

The set of protected thiols exemplified here was chosen to illustrate clean, high-yield synthetic routes to introduce the thiol moiety onto functional molecules. Molecules were selected for the importance of their functionalities and for their reactive groups available for derivatization (Scheme 2). Thus, the synthesis of protected mercaptans using an accessible phenol or alcohol group (compounds 3 and 6), a heterocyclic nitrogen atom (compound 8), an accessible carboxylic acid group (compounds 10 and 12), a terminal olefin group (compound 10), or an available halide atom (compounds 3, 8, 12, and 13) are provided as examples. Compounds 3 and 6 illustrate convenient methods to control the distance between the grafted side-group and the polymer backbone after thiol-ene coupling. Note that an 8 atom spacer (or other size) can be incorporated by replacing $H(OCH_2CH_2)_2Cl$ with commercially available $H(OCH_2CH_2)_3Cl$ or analogs in the described procedure for the synthesis of 4.

Reaction conditions for the synthesis of compounds 2-13 demonstrate highly efficient and scalable methods that can be generalized to the preparation of related compounds (in terms of the reactive groups available for derivatization). $^1$H NMR analysis of crude reaction mixtures showed that all reaction steps resulted in quantitative conversion to desired product (except synthesis of 9 and 11, for which conversion was ~90%). The clean synthetic steps made it possible to isolate products in 95-100% purity and 90-100% yield by mere use of liquid-liquid extraction/washes, and evaporation of low-boiling compounds. In some cases, further purification was achieved by recrystallization to yield analytically pure product (compounds 3, 7, 8, and 12).

Scheme 2. Synthesis of Benzoyl- or Acetyl-Protected Thiols$^a$

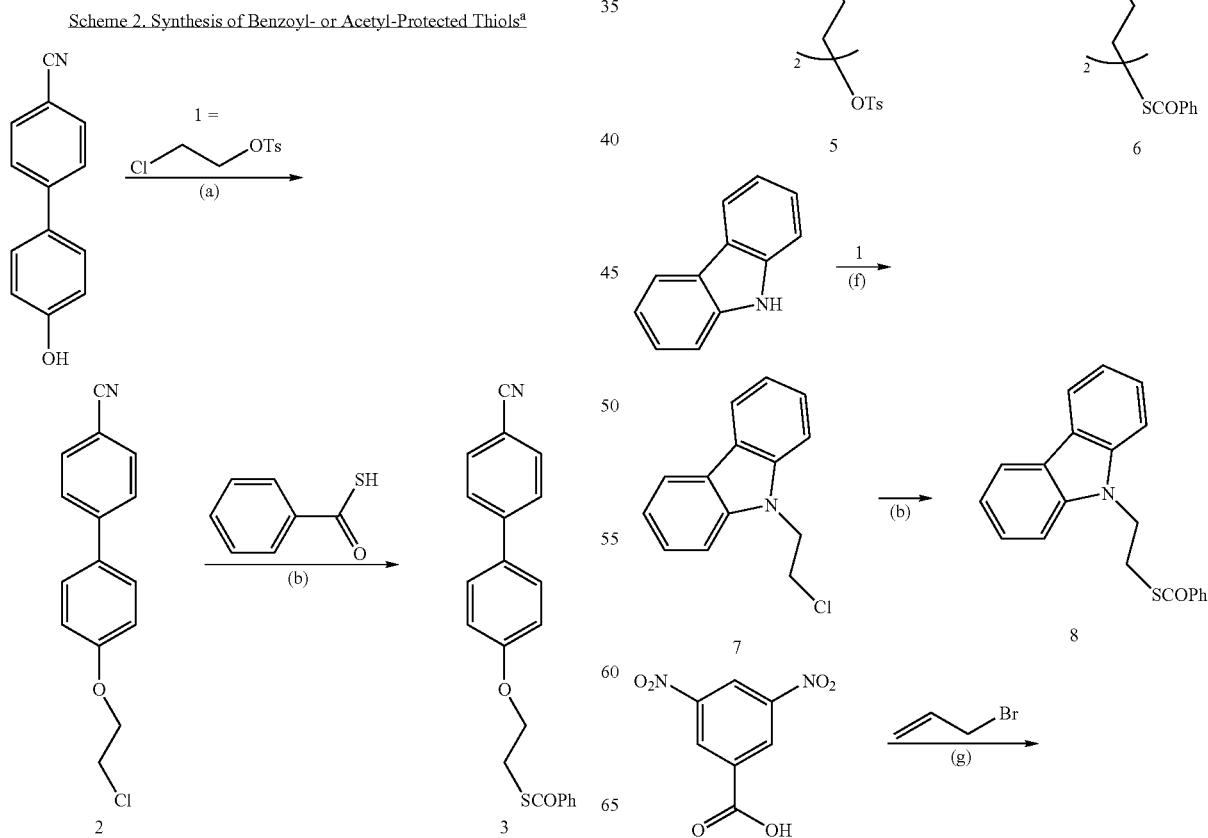

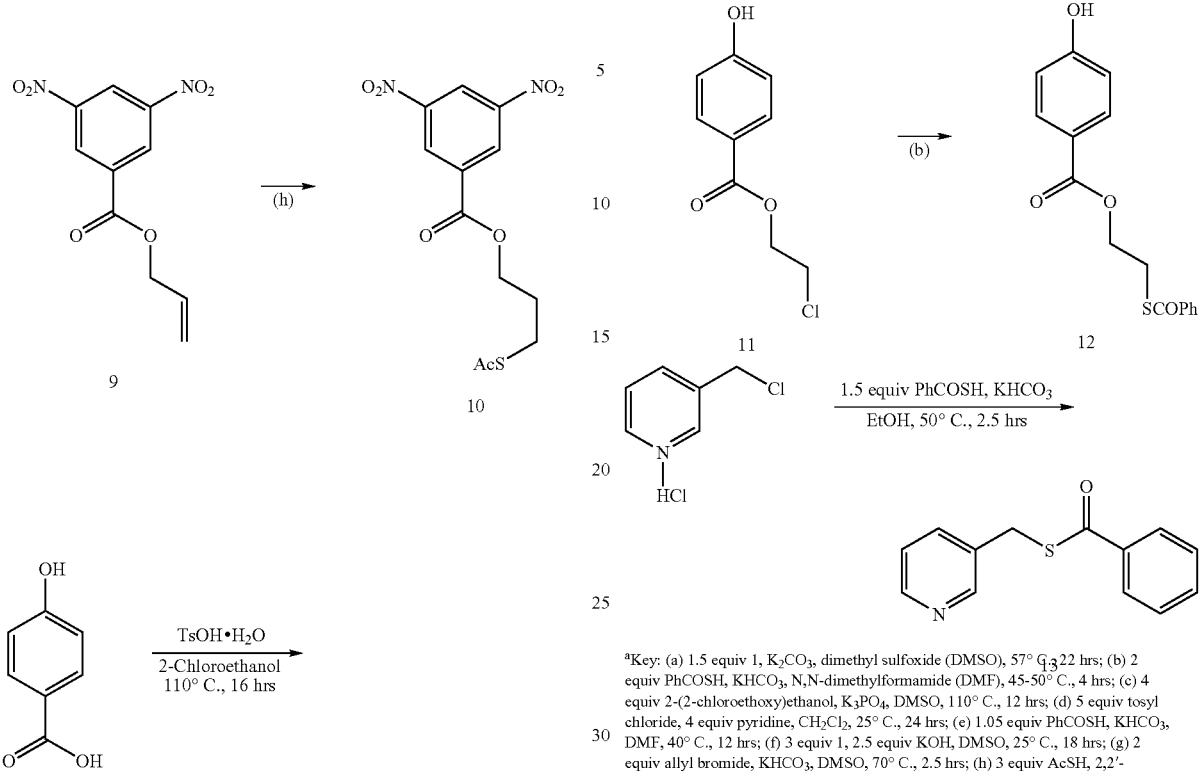

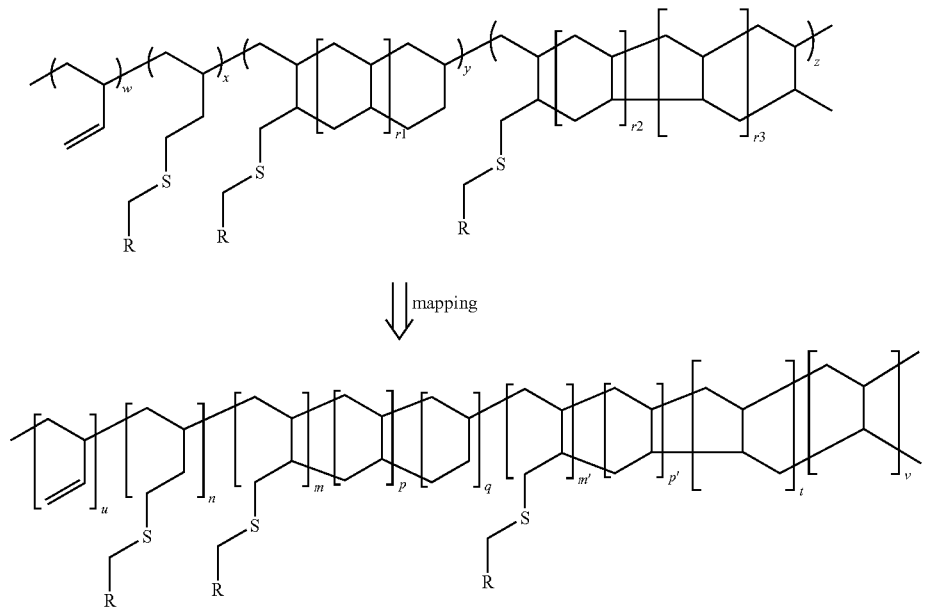

Scheme 3. General structure of functionalized 1,2-polybutadiene (1,2-PB) and calculation of the fraction of 1,2-PB repeat units that are functionalized, cyclized, and unreacted. For any cyclic or polycyclic structure of type y or z, the number of repeat units $r_1$, $r_2$ and $r_3$ can be any non-negative integers. The mapping is interpreted as follows: u is the total number of unreacted monomers in the polymer chain; p is the total number of reacted, unfunctionalized monomers involved in six-member rings "in the middle" of a polycyclic ring structure of type y; p' and v are the total number of reacted, unfunctionalized monomers involved in six member rings "to the left" and "to the right", respectively, of the five-member ring in a polycyclic structure of type z; etc. Pairs of indices (m and m', p and p') refer to groups that contribute identically to NMR spectra.

Figure 8:
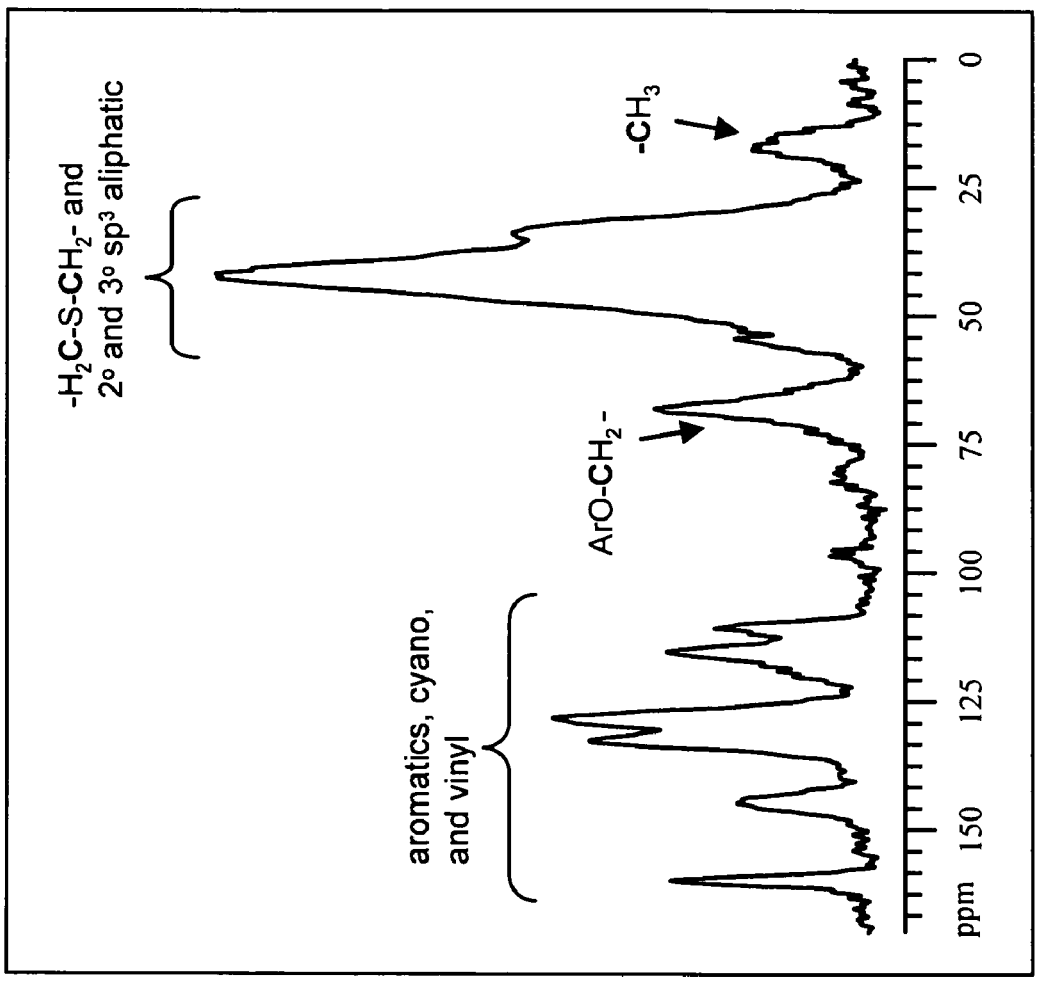
FIG. 8 shows representative solid-state $^{13}$C NMR spectrum of functionalized 1,2-polybutadiene polymer (92kPB3; refer to Table 1 and to structure at bottom of FIG. 7).
Figure 9:
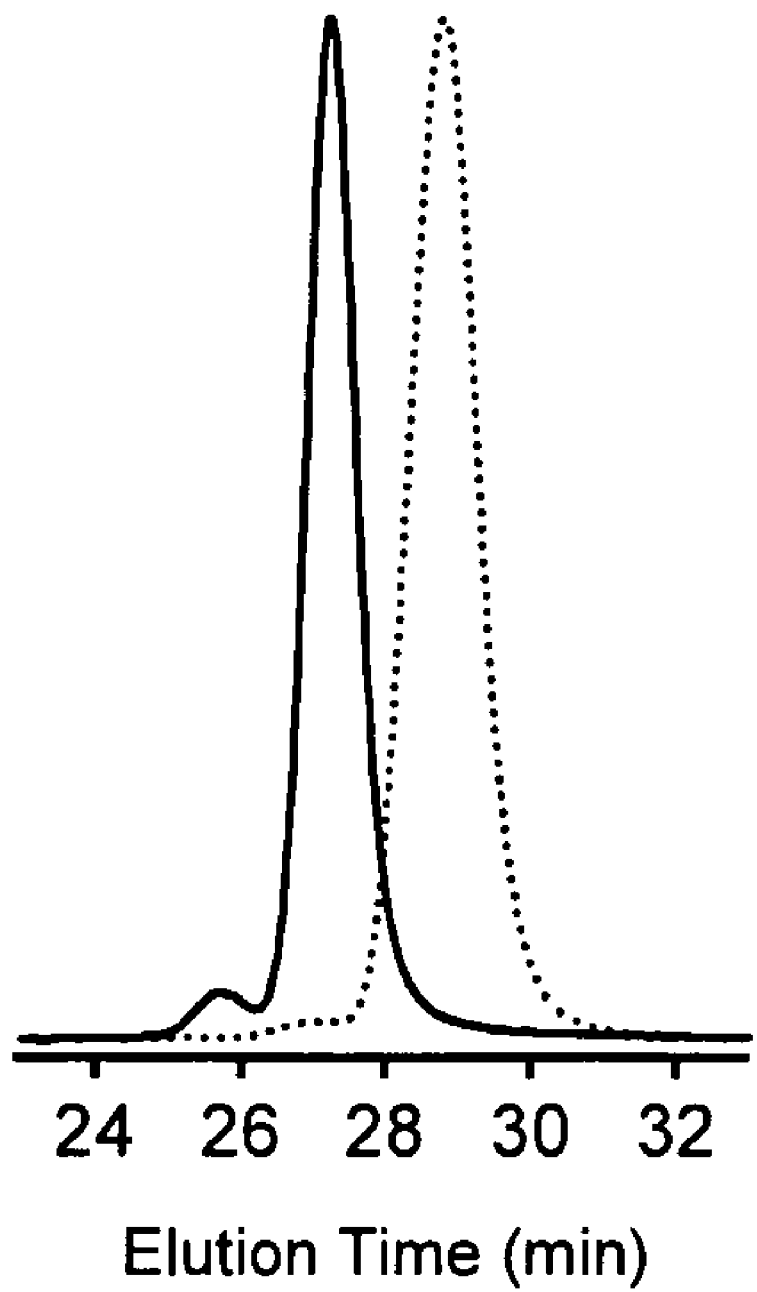
FIG. 9 shows representative gel permeation chromatography trace of functionalized 1,2-polybutadiene (1,2-PB) polymer. The solid line corresponds to 92kPB3 (refer to Table 1); the dashed line is 92 kg/mol 1,2-PB polymer.

Functionalization of 1,2-PB. Reaction conditions for 1,2-PB functionalization given in Table 1 incorporate functional side-groups while preserving the narrow molar mass distribution of the unfunctionalized polymer material (Table 1, Scheme 3, FIGS. 7-9). Depending on the application, degrees of functionalization from $\leq 1\%$ to $\geq 50\%$ are of interest; here, systematic control of functionalization ($X_{funct}$) from a few % to 40% is demonstrate d (Table 1). PB chains with very high 1,2-content tend to form cyclic adducts, which limit functionalization to $\leq 50\%$ unless very high thiol concentrations are used.[18,19] Accounting for the formation of ring structures by random cyclization of adjacent repeat units during the addition reaction, the general structure of the functionalized polymer is as shown in Scheme 3. That structure is solved by considering that either five- or six-member rings can be formed, and that polycyclic structures are possible. Note that any cyclic or polycyclic structure involves at most one five member ring (on either side of which can be fused any number of six-member rings), and that there are exactly as many methyl groups in the functionalized polymer as there are five-member rings. Let $X_{funct}$ be the fraction of reacted 1,2-PB repeat units bearing functional groups, $X_{unreact}$ be the fraction of unreacted 1,2-PB repeat units, and $X_{cycl}$ be the fraction of reacted 1,2-PB repeat units that are unfunctionalized. Thankfully, analysis of the general structure (FIG. 7) provides an unambiguous relationship between $X_{funct}$, $X_{unreact}$, $X_{cycl}$ and three quantities that are readily determined from the $^1$H NMR spectra: the relative values of the integrals of $RCH_2S$— methylene protons ($S_1$), $H_2C=CH$— alkenic protons ($S_2$), and aliphatic protons of chemical shifts below 2.2 ppm ($S_3$). In terms of the indices defined in FIG. 1, $S_1 \sim 2$ (n+m+m') and $S_2 \sim 2$ u. Furthermore, since none of the side-groups R in the present study display protons with $\delta$<2.2 ppm, $S_3 \sim [5n+4(m+m')+6(p+p'+t)+7(q+v)+3u]$. Because there are as many beginnings as ends in both y and z structures (Scheme 3, top), m=q, and m'=v; therefore, (p+p'+t+q+v)=(2$S_3$−3$S_2$−5$S_1$)/12. Thus, $X_{funct}$, $X_{unreact}$, and $X_{cycl}$ can be calculated by the expressions below without any knowledge of the relative amounts of the repeat units m, m', p, p', q, t, or v in the functionalized polymer:

$$X_{funct} = \frac{n+m+m'}{n+m+m'+p+p'+t+q+v+u} = \frac{6S_1}{S_1+3S_2+2S_3}$$

$$X_{unreact} = \frac{u}{n+m+m'+p+p'+t+q+v+u} = \frac{6S_2}{S_1+3S_2+2S_3}$$

$$X_{cycl} = 1 - X_{funct} - X_{unreact}$$

Functional polymer could also be obtained in a two-step polymer modification procedure, by thiol-ene addition of β-mercaptoethanol (BME), followed by esterification of the incorporated hydroxyl groups with a suitable acyl halide (Scheme 4, Table 2). The narrow polydispersity of well-defined polymer material could also be preserved throughout this process (Table 2), so that the procedure offers a useful alternative to direct coupling of a thiol derivative when an acyl chloride compound featuring the desired functionality is readily accessible.

Scheme 4. Alternative Route to New Functional Derivatives of 1,2-Polybutadiene by Thiol-Ene Coupling Using an Acyl Chloride RCOCl.

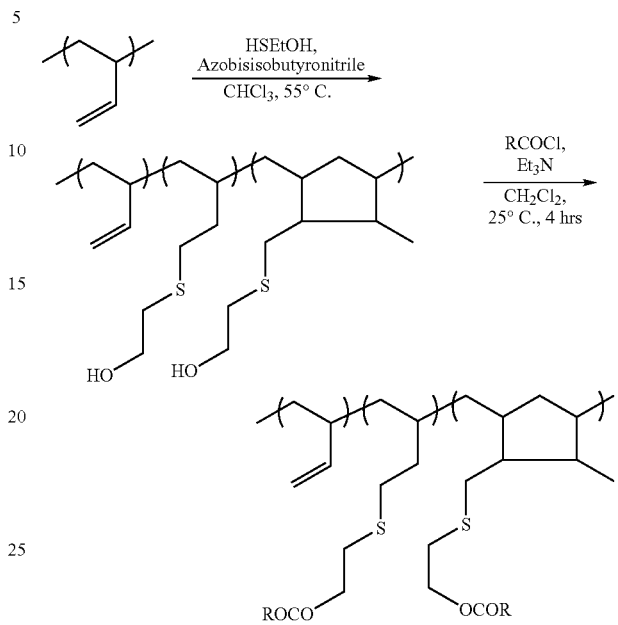

Molecular Structure of Functionalized 1,2-PB Polymer. The potential to form cyclic structures follows from the reaction mechanism. The addition reaction is initiated by abstraction of a thiol hydrogen by a cyanopropyl free radical. The resultant thiyl radical (RS.) adds to a double bond of 1,2-PB in anti-Markovnikov fashion[16-18], generating a polymeric alkyl radical (e.g. Structure I in Scheme 3). As shown in the figure, transfer of hydrogen from another thiol molecule completes the addition reaction (Structure II) and regenerates a new RS. participant; alternatively, intramolecular reactions of I compete with hydrogen transfer to form Structures III and IV. As evidence for the formation of ring structures by intramolecular cyclization, Schlaad[18,19] pointed to incomplete functionalization at full conversion of double bonds using 1,2-PB-block-poly(ethylene oxide) as starting material, i.e. typically only 60-80 functional side-group were found for every 100 reacted 1,2-PB repeat units. Direct evidence of cyclization is seen in the $^1$H NMR spectra in the present study (bottom trace in FIG. 7 and FIG. 1-6): the broad peaks below 2.2 ppm are not consistent with the structures of repeat units w and x in Scheme 3, but consistent with cyclohexyl or cyclopentyl proton signals. Further, the observed multiple peaks assignable to the $RCH_2SCH_2$— protons of the functionalized polymer (protons 4, 5, 6, FIG. 7) cannot be explained in the absence of cyclization, but are consistent with a combination of the repeat units n, m, and m' in Scheme 3.

Scheme 5. Possible reaction pathways for radical thiol addition to 1,2-polybutadiene and competing cyclization reactions.

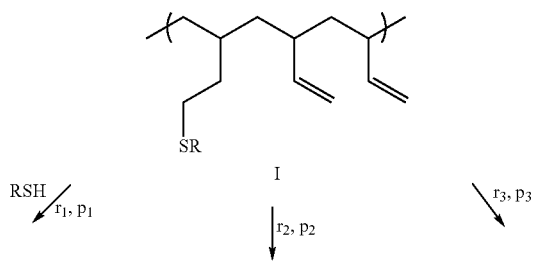

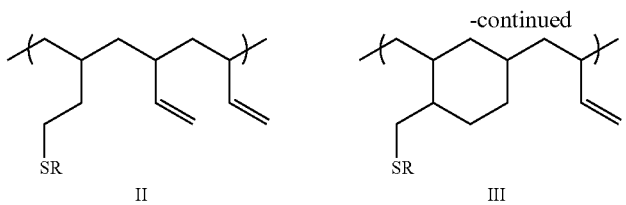

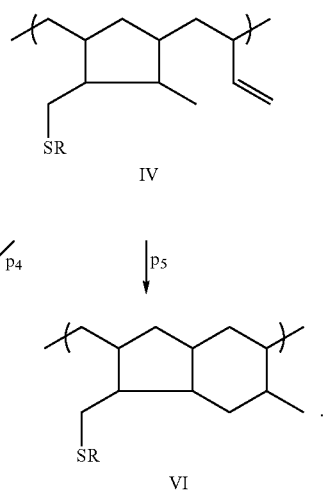

Figure 7:
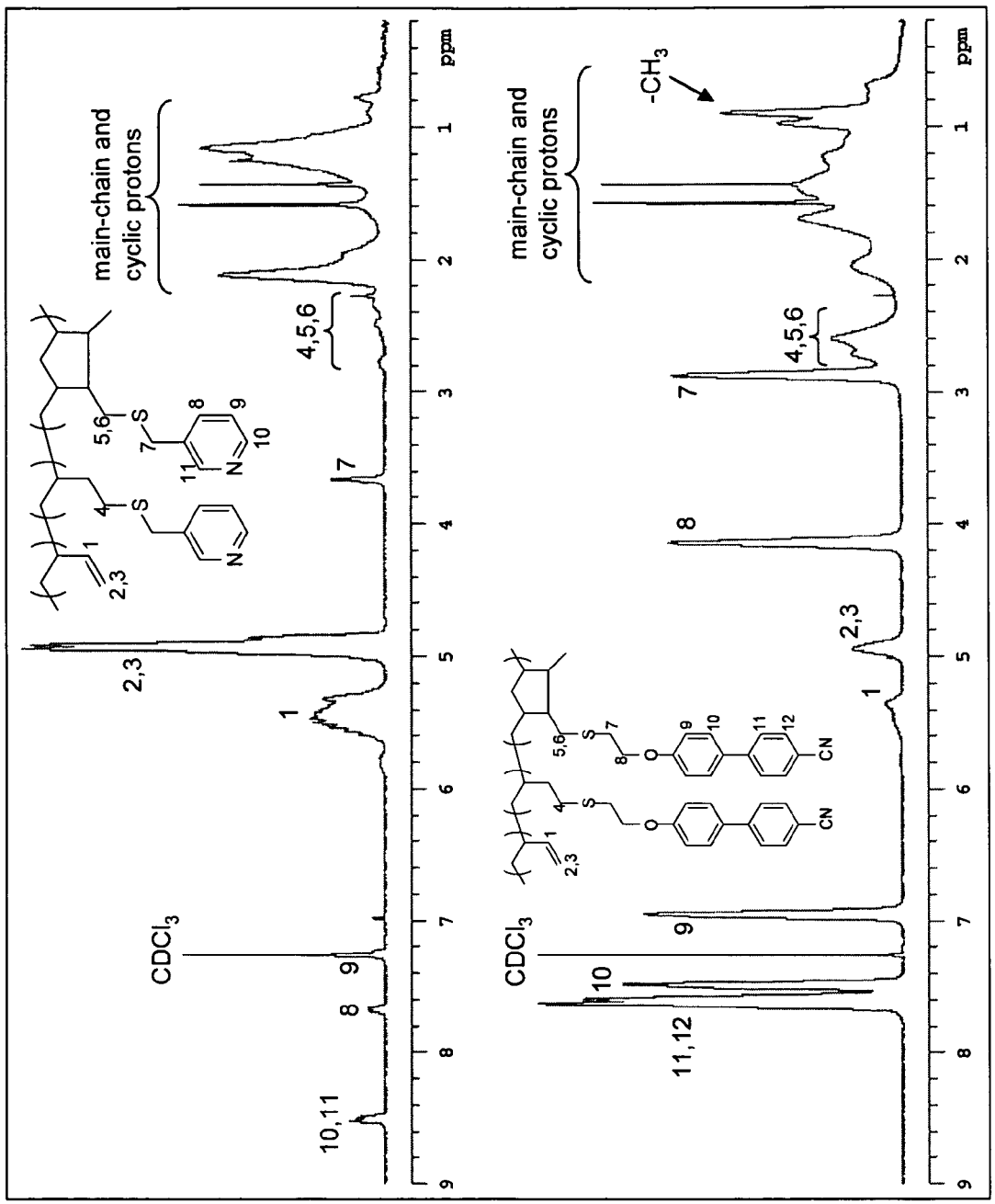
FIG. 7 is representative $^1$H NMR spectra of functionalized 1,2-polybutadiene polymers (92kPB13, top trace, and 92kPB3, bottom trace; refer to Table 1). Note that the two protons of the RCH$_2$SCH$_2$— methylene groups directly attached to ring structures are not equivalent and hence give separate signals. In both spectra, visible peaks at $\delta$=6.97, 2.27, and 1.43 ppm belong to 2,6-ditert-butyl-4-methylphenol (BHT), and peaks near $\delta$=1.6 ppm correspond to water.

The question now arises whether radical I in Scheme 4 predominantly forms III or IV during cyclization. Based on the relative thermodynamic stability of secondary versus primary radical intermediates, Schlaad and coworkers[18] have suggested that six-member rings (III) should be preferred over their five-member counterparts (IV); however, experimental results discussed in the next few paragraphs give instead evidence to the contrary. First, the data presented here reveals a high content of five-member rings in reacted polymer. NMR analysis of our product for highly functionalized chains shows i) a strong peak around 17 ppm in the solid state $^{13}$C spectra (FIG. 8), and ii) a strong signal at 1-0.9 ppm in the $^{1}$H NMR spectra (FIG. 7, bottom). Both these signals are consistent with the methyl group of structure v in Scheme 5. Since there are exactly as many five-member rings as methyl groups in the functionalized polymer, it is deduced that a large number of unfunctionalized, reacted monomers cyclized into five-member rings.

Next, literature results[22,30] on the radical addition of primary alkyl iodides to 1,2-PB and α,ω-alkadienes provides further evidence. Although the initiation, addition, and transfer steps for RI versus RSH radical addition involve molecules of substantially different reactivity, the intermediate radicals involved in intramolecular cyclization have essentially the same structure (i.e. replace RS by R in structures I, III, and IV of Scheme 5). Thus, the relative rates of formation of five-versus six-member ring structures should be comparable. According to reports on the radical addition of perfluoroalkyl iodides to 1,2-PB[22] and 1,6 heptadiene[30], intramolecular reaction of polymer radical I is expected to form primarily five-, instead of six-, member cyclic intermediates (structure IV rather than III).

Figure 10:
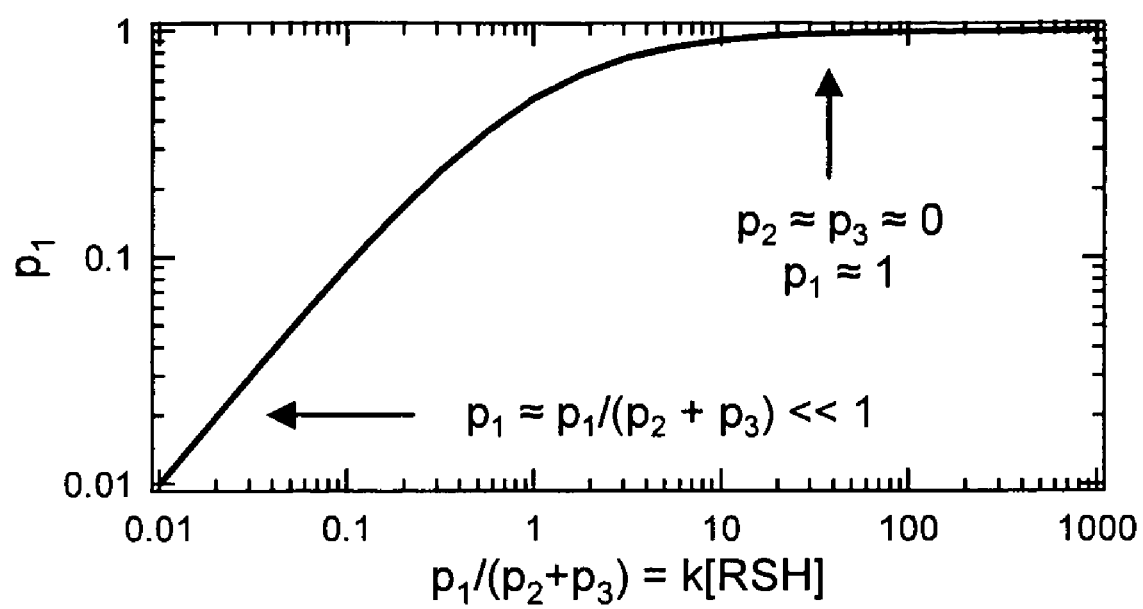
FIG. 10 shows the fraction $p_1$ of species I (Scheme 4) to proceed to abstract hydrogen from RSH as a function of [RSH] exhibits a linear increase at low concentration and saturates above a characteristic concentration that corresponds to $p_1/(p_2+p_3) \approx 10$.

In order to make further progress, let us now inquire about the competition between H-abstraction by I (forming II) versus cyclization of I (to form III or IV). This competition depends both on thiol concentration and steric hindrance to H-abstraction by I. Let $r_1$, $r_2$, $r_3$ and $p_1$, $p_2$, $p_3$ be the reaction rates and transitional probabilities for the pathways I→II, III, or IV, respectively (Scheme 4). At low extents of conversion, steric hindrance to H-abstraction by I is small, so that $p_1/(p_2+p_3)=r_1/(r_2+r_3)\sim[RSH]$. Schlaad's data[18] demonstrated that at sufficiently high [RSH] (on the order of 10 M), H-abstraction was predominant, and degrees of functionalization as high as $X_{funct}$=85% could be obtained. Only marginal increases in $X_{funct}$ could be achieved with increasing [RSH] above 10 M, but Schlaad observed that cyclization began to compete noticeably at [RSH]≦5 M. It is now shown that these observations indicate that $p_1/(p_2+p_3)\sim10$ at 5 M RSH. At low extents of reactions, $p_1/(p_2+p_3)=p_1/(1-p_1)$ is proportional to [RSH]. The proportionality constant pertinent to low extents of conversion is denoted by k, i.e. $p_1/(p_2+p_3)=k[RSH]$, giving $p_1=k[RSH]/(1+k[RSH])$. At very high thiol concentrations (k[RSH]>>1 in FIG. 10), $p_1=1$ and $p_2=p_3=0$, so that there is no cyclization. Upon decreasing [RSH], cyclization begins to compete noticeably. The onset of competition as seen in FIG. 10 occurs at $k[RSH]=p_1/(p_2+p_3)\sim10$, where $p_1\approx0.9$.

The above result has important implications for the relative formation of five- vs. six-member rings. First, the finding that $k\sim O(1\ M^{-1})$ leads immediately to the realization that under the functionalization conditions used in the present study ([RSH]~O($10^{-1}$ M or less), radical I (FIG. 5) primarily undergoes intramolecular reaction, i.e. $p_1\approx p_1/(p_2+p_3)\sim O(10^{-1}$ or less). Second, the fact that very little of radical I proceeds to abstract H from RSH under these conditions suggests that likewise very little of radical III would abstract H under the same conditions (judging reactivity based on structure similarity). Therefore, if, as Schlaad suggests, intramolecular cyclization of I led primarily to the six-member rings III, the similarity of I and III would cause III to propagate a ladder of many six-member cycles prior to concluding with H-abstraction from RSH. In that case, the functionalized polymer here would then display i) very high ratios of cyclization to functionalization, $X_{cycl}/X_{funct}>>1$, and ii) very few five-member rings. Both these results are contrary to the observations.

The data is consistent with the following predominant pathway: I→IV→V (Scheme 4) for thiol concentrations on the order of $10^{-2}$-$10^{-1}$ M. That is, I cyclizes predominantly, and five-member rings are more likely, but IV abstracts hydrogen predominantly. Note that such different relative reactivity for radicals I and IV are reasonable based on their structures. Further, this reaction pathway successfully explains the observed ratios of $X_{funct}/X_{cycl}$ in the relatively narrow range of 0.65-1 (Tables 1 and 2) over the >1 order of magnitude range of thiol concentration spanned by our experiments. If the reaction proceeded exclusively from 1 to IV to V ($p_1=p_2=p_5=0$), then $X_{funct}/X_{cycl}=1$ and the polymer structure would consist exclusively of unreacted 1,2 units and functionalized five-member rings. In reality, deviations from $p_2=0$ or $p_{5=0}$ account for values of $X_{\mathit{funct}}/X_{\mathit{cycl}}$ smaller than 1, and deviation from $p_1=0$ account for values of $X_{\mathit{funct}}/X_{\mathit{cycl}}$ larger than 1. Increasing [RSH] increases $p_1$, leading to a greater number of acyclic functionalized units. The general predominant polymer structure is therefore the one given in Scheme 1.

Direct or Indirect Functionalization? The utility of indirect functionalization by esterification of 2-hydroxyethylthio-modified PB (Scheme 4) is somewhat limited by the high reactivity of acyl halides, which renders them incompatible with a number of important functional groups and working conditions. Furthermore, our experience with polymers that are susceptible to cross-linking (such as high MW 1,2-PB) indicates that best results are typically achieved by minimizing the number of synthetic steps involving macromolecules. Finally, the time invested in the synthesis of protected thiols is easily regained in subsequent tailoring of polymer properties by quicker adjustments in the number density of grafted side-groups. Thus, in the research reported here, it is seen that direct polymer functionalization according to Scheme 1 is preferable in most cases. However, indirect functionalization according to Scheme 4 becomes useful when i) a suitable acyl halide is commercially available, and/or ii) Scheme 1 fails for one reason or another; e.g. due to unsatisfactory deprotection of a suitable thiol. For instance, deprotection of compound 10 to give the corresponding mercaptan did not give acceptable results due to apparent partial reduction of the nitro groups.

Choice of Protecting Group. The motivation for using protected thiols arises from issues of safety, yield, efficiency, and product stability. Direct preparation of thiols can be achieved by addition of hydrogen sulfide ($H_2S$) to alkenes, or by substitution of alkyl halides with hydrogen sulfide or hydrosulfide ($HS^-$). These methods have the following disadvantages: first, both hydrogen sulfide and hydrosulfide present considerable health hazards, and second, sulfide byproducts are usually formed in significant amounts[27,31]. Alternatively, the thiol functionality can be incorporated indirectly using other sulfur-containing compounds such as thiolcarboxylic acids, thiourea, or the thiolsulphate ion, followed by bond cleavage via e.g. hydrolysis of the intermediates to generate the desired mercaptan[31]. The extra step required by any indirect method is balanced by the advantages of cleaner, less wasteful reactions, and the use of less toxic reagents. Because thiols are prone to oxidation (e.g. in air on standing), storage of protected thiols is also often considered a wiser choice.

Figure 11:
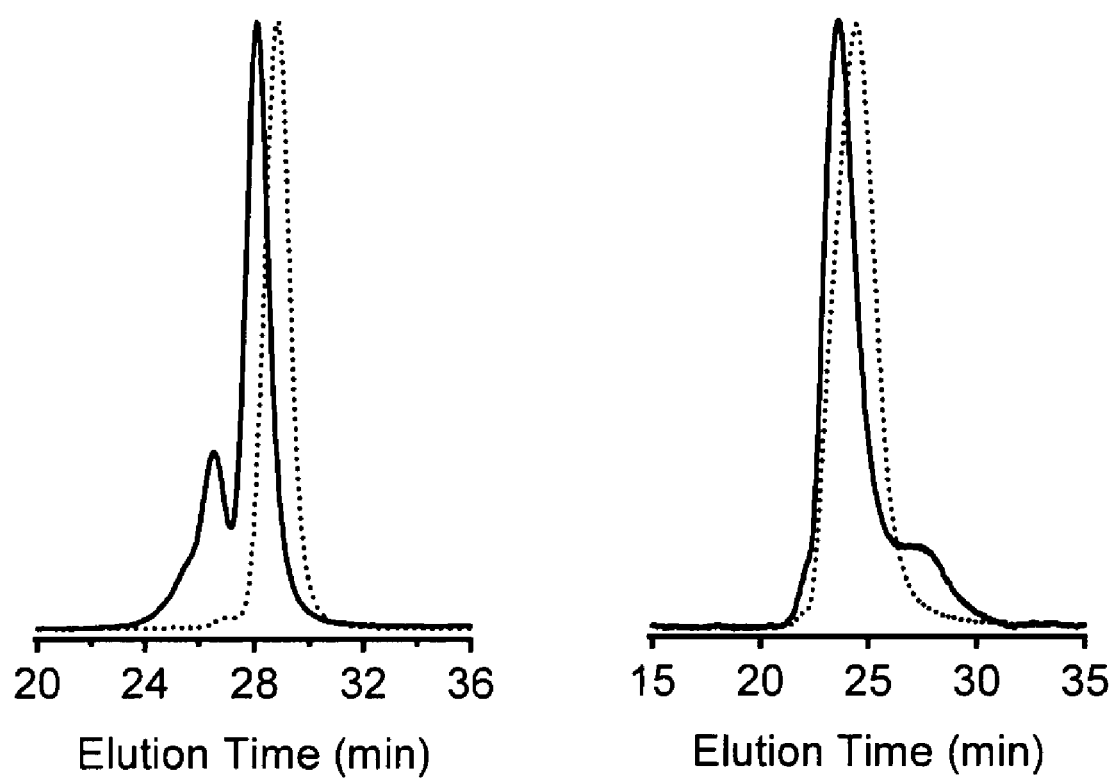
FIG. 11 shows crosslinking (left) and chain scission (right): gel permeation chromatography traces of 1,2-polybutadiene functionalized by reaction in the presence of dibenzoyl disulfide (solid line, left, 92kPB16), and in a one pot synthesis after deprotection of triphenylmethyl sulfide derivatives (solid line, right, 820kPB14). The dashed lines correspond to polymer starting materials.

Based on adverse side reactions that occur with the triphenylmethyl(trityl) group, it was necessary to turn to other protecting groups. The widespread use of the trityl group[32] reflects the ease by which it is first incorporated by substitution of halides using triphenylmethyl mercaptan, and the ease with which it is quantitatively removed (<2 hours in DCM at room temperature in the presence of TFA and triethyl- or triisopropylsilane[33-36]). The current interest in the trityl sulfide group was generated by the hope that both deprotection of the sulfide and addition of the resultant thiol to PB could be successfully carried out in one pot by using chloroform as the solvent (procedure described below). Unfortunately, experiments with 9-[2-(triphenylmethyl)thio]ethyl]carbazole (14) showed that although both deprotection and addition reactions proceeded as desired, unacceptable degradation of the polymer also occurred under such conditions (FIG. 11, right). It is also worth noting that triphenylmethyl mercaptan is a comparatively expensive reagent for the introduction of the thiol functionality.

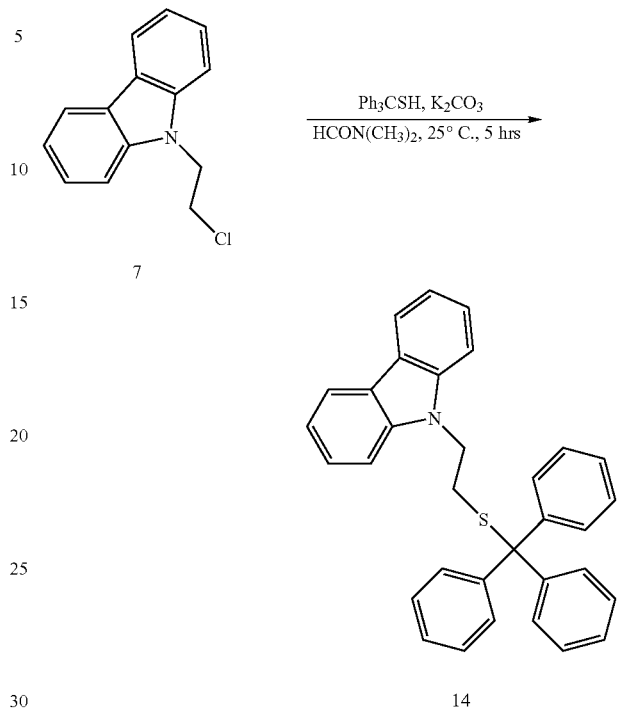

Scheme 6. Synthesis of Trityl-Protected 9-(2-Mercaptoethyl)carbazole

Thioesters have been used extensively in the past as protecting groups of the thiol functionality, with more or less success towards selective deprotection based on the reagents and method used[37]. In saccharide synthesis, thioester groups have been reported to be removed under mild conditions, i.e. in <2 hours at room temperature hydrazine acetate in DMF[38-40]. Oxygen esters were reported to be resistant to hydrolysis under these conditions. In this work, it was found that thioacetic acid and thiobenzoic acid were essentially equivalent in reactivity, but that thiobenzoic acid offers the advantage of simpler purification of the thioester product due to differences in both solubility and melting point between products and impurities. For instance, the higher molecular weight products obtained with PhCOSH were usually solid compounds amenable to recrystallization.

Synthetic Crossroads for the Introduction of the Thioester Functionality. Thioesters can be generated using thioacetic acid or thiobenzoic acid either from nucleophilic displacement of a leaving group or from radical addition to a terminal alkene (Scheme 2). Reaction of a halide or tosylate is considerably more convenient than reaction of an alkene, since the nucleophilic displacement i) does not require oxygen free conditions, and ii) essentially does not generate any impurities. Indeed, quantitative radical reaction of alkenes (e.g. synthesis of 10) is accompanied by the formation of radical termination products (0.05 to 0.3 molar equivalent) which can greatly complicate the purification process.

In some cases a leaving group (e.g. synthesis of 13) or alkene may be directly available, otherwise they can be introduced in one of the following ways: i) alcohols can be converted into good leaving groups by tosylation (e.g. synthesis of 5), ii) carboxylic acids can be reacted by Fisher esterification with e.g. 2-chloroethanol (e.g. synthesis of 11), and iii) nucleophiles can be alkylated with, for instance, allyl bromide (e.g. synthesis of 9) or 2-chloroethyl-p-toluenesulfonate (compound 1, e.g. synthesis of 2 or 7). The following considerations affect decision making regarding alkylation of nucleophiles. On the one hand, allyl bromide is considerably more reactive and available than 1, and its reaction with nucleophiles proceeds cleanly (in contrast, care must be taken in choosing reaction conditions with compound 1 to prevent bisubstitution and minimize elimination). On the other hand, the use of allyl bromide suffers in the conversion of the resulting alkene to the desired protected thiol (e.g., 9 to 10). As noted earlier, that reaction is air sensitive, and the side-products are often difficult to separate from the desired one. As a result, the ease of conversion and purification of thioesters from halides (e.g., 3 from 2) often justify the additional care required in the coupling of 1 to the molecule of interest (e.g. 1 to 2).

Functional precursors bearing nucleophilic atoms also afford a convenient method to control the spacer length between the functional group of interest and the polymer backbone. For instance, 3, 5 and 8 atom spacers can be accessed by alkylation of a nucleophile with inexpensively available $H(OCH_2CH_2)_nCl$ (n=1, 2, 3; Wako Chemicals), followed by conversion to a protected thiol as in the synthesis of 6.

Deprotection of acetyl- or benzoyl-thioesters. In all cases (with the exception of compound 10), cleavage of thioesters was achieved in >95% yields (verified by $^1H$ NMR analysis) in 2-4 hours with hydrazine acetate in DMF at room temperature (Scheme 1, step 1.1). Significantly, it was discovered that hydrazine acetate could be generated in situ by ion exchange in DMF from considerably less expensive hydrazine hydrochloride and sodium acetate, with equally successful results.

A most compelling advantage of Scheme 1 for functionalization of PB using acetyl- or benzoyl-thioesters consists in the direct addition of the deprotected mercaptan to PB without its isolation as a purified intermediate. Extraction of the DMF reaction mixture with chloroform or DCM and subsequent washing of the organic phase (Scheme 1, step 1.2) yields in ~30 min a remarkably pure solution of the thiol in which the only impurities are small amounts of disulfide (due to exposure to air), unreacted thioester (<5% of initial amount), DMF, and moisture. Radical addition of the thiol to PB is highly tolerant of these impurities and proceeds unaffected by their presence (Table 1).

Effect of Impurities. The radical addition of mercaptans to alkenes is known to be highly tolerant of a vast array of functional groups[27]. Indeed, it was found that most impurities (such as disulfides, thioesters, solvents, water, etc.) were inconsequential during thiol-ene functionalization of PB, with the following notable exceptions. First, in one-pot reaction procedures after detritylation of triphenylmethyl sulfides, some unidentified compound(s) caused chain scission of 1,2-PB (as mentioned earlier, FIG. 11, right). Second, it was found that the presence of benzoyl disulfide (PhCOS-SOCPh) resulted in significant cross-linking. For example, use of a sample of thiobenzoic acid S-[3-(9-carbazolyl)propyl]ester (16) containing ~0.2 molar equivalent of benzoyl disulfide caused polydispersity to increase from PDI=1.07 to 1.34 at 19% functionalization (FIG. 7, left).

Implications of Extents of Cyclization for 1,2-PB. Depending on the reason for modifying the polymer, degrees of functionalization from a few % up to ~100% are of interest. Experiments show cyclization to functionalization ratios $X_{cycl}/X_{funct}$ of 1-1.5, meaning that during the course of the addition reaction nearly as many reacted monomers were functionalized as were consumed without functionalization by intramolecular cyclization. It was found to be the case for reaction conditions spanning more than one order of magnitude in thiol concentration in the range $10^{-2}<[RSH]<3\times10^{-1}$ M. That is, 1,2-PB functionalization at moderately low to very low thiol concentrations proceeds without excessive amounts of cyclization (which would be expected if radical I in Scheme 4 led primarily to six-member rings, as explained earlier). The implications of this result are two-fold. First, low target levels of functionalization can be readily achieved at low or very low [RSH], with minimal changes in the physical properties of the polymer product resulting from cyclic/polycyclic structures. This enables good control of the extent of reaction and minimizes waste of potentially highly valuable thiol reagent. Second, the result suggests an alternative synthetic strategy to using extremely high thiol concentration (on the order of 10 M!) in order to achieve high degrees of functionalization (say >70%). Taking advantage of the fact that cyclization to functionalization ratios remain in the narrow range of 1-1.5 at thiol concentrations of 0.01-0.1 M, the strategy involves synthesis of thioester compounds featuring two functional side-groups per molecule. Deprotection and addition to 1,2-PB according to Scheme 1 using thiol concentrations on the order of 0.1 M will result in incorporation of e.g. 80% side groups at 40% functionalization. This type of molecule is shown as compound 17 as shown in Scheme 7.

Scheme 7. Proposed Synthesis of a Protected Thiol Bearing Two Mesogenic Side-Groups

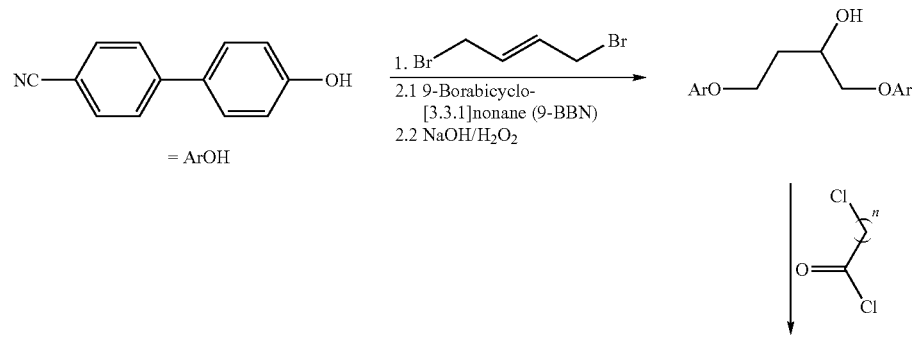

-continued

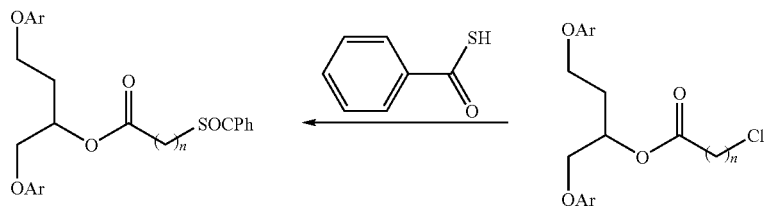

17 n = 1, 2, 3

TABLE 1

Reaction Conditions and Results for 1,2-PB Functionalization Using Protected Thiol PhCOSR

| Entry[a] | [PB] (g/mL) | [Thiol][b] | [AIBN] (g/mL) | Rxn time (hrs) | $X_{funct}$[c] % | $X_{cycl}$[c] % | $M_W$[d] (kg/mol) | PDI[d] | New $^1$H NMR peaks above 2.2 ppm for modified PB (all peaks are broad) |
|---|---|---|---|---|---|---|---|---|---|
| 92kPB3[e,g] | 0.004 | 1.6 | 0.005 | 6.2 | 40 ± 2 | 48 ± 3 | 199 | 1.07 | 7.71-7.43 (6H), 7.01-6.88 (2H), 4.22-4.08 (2H), 2.95-2.43 (4H) |
| 92kPB6[f] | 0.003 | 0.5 | 0.002 | 3.7 | 22 ± 2 | 34 ± 3 | 194 | 1.07 | 7.71-7.58 (4H), 7.54-7.46 (2H), 7.05-6.95 (2H), 4.19-4.12 (2H), 3.90-3.82 (2H), 3.77-3.67 (2H), 2.77-2.39 (4H) |
| 92kPB8 | 0.004 | 1.2 | 0.001 | 4.4 | 36 ± 2 | 41 ± 3 | 146 | 1.06 | 8.12-7.95 (2H), 7.53-7.12 (6H), 4.53-4.26 (2H), 2.95-2.72 (2H), 2.65-2.2 (2H) |
| 92kPB12 | 0.009 | 1.5 | 0.001 | 3.6 | 16 ± 1 | 18 ± 2 | 98 | 1.02 | 7.93-7.83 (2H), 7.88-7.80 (2H), 4.43-4.34 (2H), 2.87-2.44 (4H) |
| 92kPB13[e] | 0.003 | 1.9 | 0.001 | 2.0 | 4 ± 1 | 6 ± 2 | 122 | 1.07 | 8.55-8.46 (2H), 7.70-7.63 (1H), 7.28-7.22 (1H), 3.70-3.62 (2H), 2.82-2.43 (2H) |
| 820kPB3 | 0.003 | 0.3 | 0.001 | 1.5 | 4 ± 1 | 4 ± 2 | 1420 | 1.45[h] | 7.69-7.56 (4H), 7.56-7.45 (2H), 7.00-6.91 (2H), 4.19-4.10 (2H), 2.92-2.80 (2H), 2.74-2.49 (2H) |
| 820kPB8[f] | 0.004 | 1.3 | 0.002 | 3.0 | 27 ± 2 | 36 ± 3 | 1200 | 1.25 | 8.11-7.95 (2H), 7.49-7.12 (6H), 4.52-4.28 (2H), 2.94-2.71 (2H), 2.61-2.2 (2H) |
| 820kPB12[f] | 0.007 | 0.2 | 0.002 | 3.0 | 7 ± 1 | 11 ± 2 | 579 | 1.48[h] | 7.94-7.87 (2H), 6.87-6.79 (2H), 4.45-4.33 (2H), 2.88-2.41 (4H) |
| 820kPB13 | 0.007 | 0.2 | 0.002 | 2.5 | 2 ± 1 | 3 ± 2 | 1310 | 1.26 | 8.55-8.46 (2H), 7.70-7.64 (1H), 7.28-7.22 (1H), 3.68-3.62 (2H), 2.82-2.43 (2H) |

[a]Modified PB polymers were named so that the prefix corresponds to the molecular weight of the starting 1,2-PB chain (98% 1,2 content), and the suffix represents the thioester reagent (Scheme 2) used.
[b]In molar equivalents of 1,2-PB monomer units, estimated from the mass ratio of the protected thiol PhCOSR and 1,2-PB.
[c]The fraction of reacted 1,2-PB units that bear functional groups ($X_{funct}$) and that are not functionalized ($X_{cycl}$); refer to text. The reported uncertainties were calculated based on the following uncertainties for the integrals $S_1$, $S_2$, and $S_3$: the measurement of $S_3$ is ~3% accurate, and the uncertainties in $S_1$ and $S_2$ are both <1% of ($S_1 + S_2$).
[d]Measured as described in Experimental section using the Waters setup, except for polymer 92kPB12 (measurements obtained by MALLS). The 1,2-PB polymers had PDI of 1.07 and 1.26 for the 92 kg/mol and 820 kg/mol 1,2-PB chains, respectively.
[e]$^1$H NMR traces are given in FIG. 2.
[f]$^1$H NMR traces are given in the Supplementary Information section.
[g]GPC trace is given in FIG. 4.
[h]A small amount of cross-linking is believed to have occurred during workup and handling of the polymer product.

TABLE 2

Reaction Conditions and Results for 1,2-PB Functionalization Using 3,5-Dinitrobenzoyl Chloride (DNBC)

| Entry[a] | [PB] (g/mL) | [BME][b] | [AIBN] (g/mL) | Rxn time (hrs) | $X_{funct}$[d] % | $X_{cycl}$[d] % | $M_W$[e] (kg/mol) | PDI[e] | New H NMR peaks above 2.2 ppm for modified PB (all peaks are broad) |
|---|---|---|---|---|---|---|---|---|---|
| 92kPB-OH[f] | 0.03 | 0.6 | 0.002 | 1.9 | 20 ± 1 | 28 ± 2 | 151 | 1.07 | 3.77-3.65 (2H), 2.76-2.2 (4H) |
| 820kPB-OH | 0.02 | 0.4 | 0.001 | 3.0 | 15 ± 1 | 24 ± 2 | 1170 | 1.24 | 3.77-3.66 (2H), 2.76-2.3 (4H) |

| Entry[a] | [PB-OH] (g/mL) | [DNBC][c] | [Et$_3$N][c] | Rxn time (hrs) | $X_{funct}$[d] % | $X_{cycl}$[d] % | $M_W$[e] (kg/mol) | PDI[e] | New H NMR peaks above 2.2 ppm for modified PB (all peaks are broad) |
|---|---|---|---|---|---|---|---|---|---|
| 92kPB-DNB[f] | 0.02 | 3.3 | 5.0 | 4.0 | 20 ± 1 | 28 ± 2 | 158 | 1.08 | 9.24-9.20 (1H), 9.20-9.12 (2H), 4.64-4.51 (2H), 2.97-2.81 (2H), 2.81-2.41 (2H) |

TABLE 2-continued

Reaction Conditions and Results for 1,2-PB Functionalization Using 3,5-Dinitrobenzoyl Chloride (DNBC)

| 820kPB-DNB | 0.02 | 2.5 | 3.5 | 3.3 | 15 ± 1 | 24 ± 2 | 1410 | 1.28 | 9.24-9.20 (1H), 9.20-9.12 (2H), 4.65-4.51 (2H), 2.97-2.83 (2H), 2.80-2.42 (2H) |
|---|---|---|---|---|---|---|---|---|---|

[a]Modified PB polymers were named so that the prefix corresponds to the molecular weight of the starting 1,2-PB chain (98% 1,2 content), and the suffix represents the functional group added.
[b]In molar equivalents of 1,2-PB monomer units.
[c]In molar equivalents of 2-hydroxyethylthio- functionalized monomer units.
[d]The fraction of reacted 1,2-PB units that bear functional groups ($X_{funct}$) and that are not functionalized ($X_{cycl}$); refer to text. The reported uncertainties were calculated based on the following uncertainties for the integrals $S_1$, $S_2$, and $S_3$: the measurement of $S_3$ is ~3% accurate, and the uncertainties in $S_1$ and $S_2$ are both <1% of ($S_1$ + $S_2$).
[e]Measured as described in Experimental section using the Waters setup. The 1,2-PB polymers had PDI of 1.07 and 1.26 for the 92 kg/mol and 820 kg/mol 1,2-PB chains, respectively.
[f]$^1$H NMR traces are given in the Supplementary Information section.

EXPERIMENTAL

Materials and Instrumentation. Except for thiobenzoic acid (Alfa Aesar, 94%), carbazole (Aldrich, 95%), 4'-hydroxy-4-carbonitrile (TCI, 95%), thioacetic acid (Aldrich, 96%), allyl bromide (Aldrich, 97%), hydrazine monohydrochloride (Acros Organics, 98%), p-toluenesulfonyl chloride (Alfa Aesar, 98%), and p-toluenesulfonic acid monohydrate (Aldrich, 98.5%), all reagents were obtained at 99% purity from Aldrich, Alfa Aesar, or Mallinckrodt Chemicals. 2,2'-Azobis (2-methylpropionitrile) (AIBN) was recrystallized biweekly in methanol (10 mL solvent per g AIBN) and stored at 4° C.; all other reagents were used as received without further purification. Polybutadiene polymer chains (98% 1,2-content) of size 92×10$^3$ and 820×10$^3$ g/mol and narrow molecular weight distribution (of polydispersity index 1.07 and 1.26, respectively) were kindly donated by Dr. Steven Smith of Procter and Gamble Company. $^1$H and $^{13}$C NMR spectra were obtained using a Varian Mercury 300 spectrometer (300 MHz for $^1$H and 74.5 MHz for $^{13}$C); all spectra were recorded in CDCl$_3$ and referenced to tetramethylsilane. Polymer molecular weight measurements were obtained by gel permeation chromatography using one of two systems. Measurements were either carried out i) in tetrahydrofuran (THF) at 25° C. eluting at 0.9 mL/min through four PLgel 10 μm analytical columns (Polymer Labs, 10$^6$ to 10$^3$ Å in pore size) connected to a Waters 410 differential refractometer detector (λ=930 nm) or ii) in THF on two PLgel 5 μm mixed-C columns (Polymer Labs) connected in series to a DAWN EOS multiangle laser light scattering (MALLS) detector (Wyatt Technology, Ar laser, λ=690 nm) and an Optilab DSP differential refractometer (Wyatt Technology, λ=690 nm). In the former case, molecular weight measurements were analyzed based on calibration using polystyrene standards; in the latter case no calibration standards were used, and dn/dc values were obtained for each injection by assuming 100% mass elution from the columns.

Synthesis of Benzoyl- or Acetyl-Protected Thiols (Scheme 2). All reactions were monitored by $^1$H NMR spectroscopy. Analysis of reaction mixtures was generally performed by washing a ~1 mL aliquot with water and extracting organic reactants and products into an appropriate solvent, followed by solvent evaporation, and redissolving in CDCl$_3$ for NMR analysis. $^{13}$C NMR resonances of compounds 1, 3, 6, 8, 10, 12, and 13 are documented below.

2-Chloroethyl-p-toluenesulfonate (1). p-Toluenesulfonyl chloride (172 g, 0.884 mol) and pyridine (59 g, 0.75 mol) were added to 180 mL dichloromethane (DCM) in a 1 L round-bottom flask (RBF) which was placed in an ice bath for ca. 5 min. 1-Chloroethanol (40.3 g, 0.496 mol) was added slowly, and the RBF was taken out of the ice bath and left to stir at room temperature (r.t.) for 15 hrs. The reaction mixture was poured into a 1 L separatory funnel, washed twice with 300 mL water+50 mL pyridine, and again with 300 mL water+75 mL 36% wt aq. HCl (discarding the aqueous phase after each wash). Removal of the solvent at reduced pressure yielded analytically pure 1 as a faint yellow, thick syrup (116 g, 0.494 mol, 100% yield). $^1$H NMR: δ=7.81 (d, 2 aromatic H meta to CH$_3$, J=8.3 Hz), 7.37 (d, 2 aromatic H ortho to CH$_3$, J=8.3 Hz), 4.23 (t, OCH$_2$, J=5.9 Hz), 3.66 (t, CH$_2$Cl, J=5.9 Hz), 2.46 (s, CH$_3$).

4'-(2-(Benzoylthio)ethoxy)[1,1'-biphenyl]-4-carbonitrile (3). 4'-Hydroxy[1,1'-biphenyl]-4-carbonitrile (5.1 g, 0.025 mol), 2-chloroethyl-p-toluenesulfonate (1, 9.2 g, 0.039 mol), and potassium carbonate (5.3 g, 0.038 mol) were stirred at 57° C. in 100 mL dimethyl sulfoxide (DMSO) for 22 hrs, resulting in quantitative conversion to 2 (verified by NMR analysis). Potassium chloride (2.1 g, 0.028 mol) was added to the reaction mixture, which was stirred 3 hrs at 85° C. to convert the excess 1 into dichloroethane. The reaction mixture was poured into a 1 L separatory funnel containing 300 mL water and extracted with 200 mL of 2-butanone (MEK). The aqueous phase was extracted with another 300 mL MEK, and the organic extracts were combined and washed 3 times with 300 mL water. Finally, solvent and dichloroethane were evaporated under reduced pressure at 80° C. to give 2 (6.4 g, 0.025 mol, 100% yield) as a brown-orange syrup which solidifies upon cooling. To the previous product in 100 mL N,N-dimethylformamide (DMF) in a 250 mL RBF were added thiobenzoic acid (7.3 g, 0.050 mol) and potassium bicarbonate (6.8 g, 0.068 mol), and the mixture was stirred at r.t. until CO$_2$ effervescence ceased, then at 45° C. for 4 hrs. The reaction mixture was transferred to a 1 L separatory funnel containing 250 mL water, extracted with 400 mL ethyl acetate, and the organic phase was washed twice with 250 mL water before solvent removal under reduced pressure. The crude product was purified by dissolving in 300 mL ethanol at 90° C. (under slight pressure), and allowing to recrystallize by slowly cooling to r.t., then by letting stand overnight at 4° C. Filtration of the crystals and removal of solvent under reduced pressure gave analytically pure 3 as ultra-fine, pale brown needles (7.9 g, 0.022 mol, 88% overall yield in 2 steps). $^1$H NMR: δ=8.02-7.96 (m, 2 aromatic H ortho to COS), 7.72-7.43 (m, 3 aromatic H meta and para to COS, 4 aromatic H ortho and meta to CN, and 2 aromatic H meta to OCH$_2$), 7.05 (d, 2 aromatic H ortho to OCH$_2$, J=8.7 Hz), 4.25 (t, OCH$_2$, J=6.6 Hz), 3.50 (t, SCH$_2$, J=6.6 Hz).

4'-(2-(2-(Benzoylthio)ethoxy)ethoxy) [1,1'-biphenyl]-4-carbonitrile (6). 4'-Hydroxy[1,1'-biphenyl]-4-carbonitrile (4.9 g, 0.024 mol), 2-(2-chloroethoxy)ethanol (12.7 g, 0.101 mol) and potassium phosphate tribasic (K$_3$PO$_4$.xH$_2$O, 22 g at ~25% wt water, 0.078 mol) were stirred at 110° C. in 150 mL DMSO for 12 hrs, resulting in quantitative conversion to 4 (verified by NMR analysis). The reaction mixture was poured into a 1 L separatory funnel containing 200 mL chloroform and washed 5 times with 400 mL water to remove all of the chloroalcohol. The resultant organic phase was dried with $MgSO_4$, filtered, and the solvent was removed under reduced pressure at 60° C. to afford analytically pure 4 (6.5 g, 0.023 mol, 96% yield) as a pale yellow-orange syrup which solidifies upon cooling. To this product in 100 mL DCM at 0° C. were added p-toluenesulfonyl chloride (22.2 g, 0.115 mol) and pyridine (7.2 g, 0.091 mol), after which the reaction vessel was allowed warm up to and left to stir at r.t. for 24 hrs. The reaction mixture was transferred to a 500 mL separatory funnel, washed twice with 150 mL water+25 mL pyridine, and again with 150 mL water and 40 mL 36% wt aq. HCl (discarding the aqueous phase after each wash). The organic phase was again dried with $MgSO_4$, filtered, and the solvent was removed under reduced pressure at 40° C. to yield analytically pure 5 (9.5 g, 0.022 mol, 95% yield), which was finally reacted to generate 6 as follows. To 1.96 g (4.5 mmol) of the said product in 40 mL DMF were added thiobenzoic acid (0.69 g, 4.7 mmol, 1.05 equiv.) and potassium bicarbonate (1.0 g, 10 mmol), and the mixture was stirred at r.t. until $CO_2$ effervescence ceased, then at 40° C. for 12 hrs. The reaction mixture was transferred to a 500 mL separatory funnel containing 200 mL water, extracted with 100 mL ethyl acetate, and the organic phase was washed three additional times with 200 mL water, dried with $MgSO_4$, and gravity filtered before solvent removal at 80° C. under reduced pressure to give analytically pure 6 as an orange syrup which crystallizes upon cooling (1.80 g, 4.5 mmol, 91% overall yield in 3 steps). $^1$H NMR: $\delta$=8.00-7.93 (m, 2 aromatic H ortho to COS), 7.72-7.39 (m, 3 aromatic H meta and para to COS, 4 aromatic H ortho and meta to CN, and 2 aromatic H meta to $OCH_2$), 7.02 (d, 2 aromatic H ortho to $OCH_2$, J=8.7 Hz), 4.19 (t, $ArOCH_2$, J=4.8 Hz), 3.90 (t, $ArOCH_2CH_2$, J=4.8 Hz), 3.79 (t, $SCH_2CH_2$, J=6.5 Hz), 3.33 (t, $SCH_2CH_2$, J=6.5 Hz).

Thiobenzoic acid S-[2-(9-carbazolyl)ethyl]ester (8). Carbazole (15.2 g, 0.086 mol), 2-chloroethyl-p-toluenesulfonate (1, 60.2 g, 0.256 mol), and potassium hydroxide (88% wt pellets, 13.7 g, 0.215 mol) were stirred at r.t. in 300 mL DMSO for 18 hrs, resulting in quantitative conversion to 7 (verified by NMR analysis). Trichloroacetic acid (TCA, 22 g, 0.135 mol) and potassium chloride (20 g, 0.268 mol) were added to the reaction mixture, which was stirred 4 hrs at 100° C. to convert the excess 1 to dichloroethane. After titration of the excess TCA by potassium bicarbonate (15.5 g, 0.155 mol), the reaction mixture was poured into a 1 L separatory funnel containing 180 mL water and extracted with 300 mL chloroform. The organic phase was washed twice with 400 mL water, the solvent was evaporated under reduced pressure, and the crude product was purified by dissolving in 475 mL boiling ethanol and allowing to recrystallize at r.t. overnight, yielding analytically pure 7 (16.5 g, 0.072 mol, 83% yield) after filtration and solvent removal. To 6.8 g (0.030 mol) of this product in 110 mL DMF were added thiobenzoic acid (8.9 g, 0.061 mol) and potassium bicarbonate (8.0 g, 0.080 mol); the mixture was swirled with gentle heating until $CO_2$ effervescence ceased, then allowed to react 4 hrs at 50° C. The reaction mixture was poured into a 500 mL separatory funnel containing 100 mL water, extracted with 100 mL chloroform, and the organic phase was washed twice with 150 mL water before solvent removal under reduced pressure. The crude product was purified by first dissolving in 35 mL hot chloroform, adding 200 mL boiling ethanol, and allowing to recrystallize overnight at r.t. Filtration of the crystals and removal of solvent under reduced pressure gave analytically pure 8 as very fine, orange-pink needles (8.3 g, 0.025 mol, 70% overall yield in 2 steps). $^1$H NMR: $\delta$=8.10 (d, 2 carbazole H, J=7.5 Hz), 8.03-7.96 (m, 2 aromatic H ortho to COS), 7.64-7.57 (m, 3 aromatic H meta and para to COS), 7.54-7.43 (m, 4 carbazole H), 7.30-7.21 (m, 2 carbazole H), 4.55 (t, $NCH_2$, J=7.8 Hz), 3.44 (t, $SCH_2$, J=7.8 Hz).

3,5-Dinitrobenzoic acid 3-(acetylthio)propyl ester (10). Potassium bicarbonate (7.2 g, 0.072 mol) was added to 3,5-dinitrobenzoic acid (10.0 g, 0.047 mol) in 150 mL DMSO in a 500 mL RBF, and the slurry was swirled with gentle heating until $CO_2$ effervescence ceased. Allyl bromide (11.8 g, 0.095 mol) was added next, and the RBF was placed in an oil bath to stir at 70° C. for 2.5 hrs. The reaction mixture was poured into a 1 L separatory funnel containing 250 mL chloroform and washed twice with 400 mL water (discarding the aqueous phase after each wash), yielding 9 (10.7 g, 0.042 mol, 91% yield) in >99% purity after removal of allyl bromide and solvent at 80° C. under reduced pressure. To this product in 100 mL toluene was added thioacetic acid (9.8 g, 0.124 mol), and the reaction was carried out at 85° C. with argon purge via radical mechanism using AIBN as the initiator (0.70 g, 4.3 mmol, in 0.175 g increments at 1 hr intervals). After 6 hrs the reaction mixture was poured into a 1 L separatory funnel containing 16 g sodium bicarbonate ($NaHCO_3$, 0.19 mol) in 300 mL water, extracted with 100 mL chloroform, and the organic phase was washed twice with 300 mL water before solvent removal under reduced pressure. The crude product was purified by washing four times in 50 mL hexane at 60° C., yielding 10 in >99% purity as a viscous, dark brown syrup (9.1 g, 0.028 mol, 59% overall yield in 2 steps). $^1$H NMR: $\delta$=9.24 (t, 1 aromatic H para to $CO_2$, J=2.1 Hz), 9.19 (di 2 aromatic H ortho to $CO_2$, J=2.1 Hz), 4.52 (t, $OCH_2$, J=6.3 Hz), 3.07 (t, $SCH_2$, J=6.9 Hz), 2.37 (s, $CH_3$), 2.15 (tt, $OCH_2CH_2CH_2S$, J=6.9, 6.3 Hz).

4-Hydroxybenzoic acid 2-(benzoylthio)ethyl ester (12). 4-Hydroxybenzoic acid (10 g, 0.072 mol) and 1-chloroethanol (60 g, 0.73 mol) were reacted in the bulk at 110° C. for 16 hrs with p-toluenesulfonic acid monohydrate (2.7 g, 0.014 mol) as catalyst. The reaction mixture was transferred to a 500 mL separatory funnel containing 5 g sodium bicarbonate in 125 mL water, extracted with 150 mL ethyl acetate, and the organic phase was washed 4 times with 125 mL water before solvent removal under reduced pressure, yielding 11 in ca. 97% purity (13 g, 0.063 mol, 88% yield). To this product in 100 mL DMF were added thiobenzoic acid (18 g, 0.12 mol) and potassium bicarbonate (16 g, 0.16 mol), and the mixture was stirred at r.t. until $CO_2$ effervescence ceased, then at 50° C. for 4 hrs. The reaction mixture was poured into a 500 mL separatory funnel containing 100 mL water, extracted with 100 mL chloroform, and the organic phase was washed 3 times with 150 mL water before solvent removal at reduced pressure. The crude product was finally purified by first dissolving in 50 mL hot chloroform, adding 25 mL boiling hexane, and allowing to recrystallize overnight in the freezer. Filtration of the crystals and removal of the solvent under reduced pressure gave analytically pure 12 as a pink powder (14.5 g, 0.048 mol, 67% overall yield in 2 steps). $^1$H NMR: $\delta$=8.02-7.93 (m, 2 aromatic H ortho to $CO_2$ and 2 aromatic H ortho to COS), 7.59 (tt, 1 aromatic H para to COS, J=7.5, 1.2 Hz), 7.51-7.42 (m, 2 aromatic H meta to COS), 6.87 (d, 2 aromatic H meta to $CO_2$, J=8.7 Hz), 5.8 (br, ArOH), 4.50 (t, $OCH_2$, J=6.5 Hz), 3.47 (t, $SCH_2$, J=6.5 Hz). Thiobenzoic acid S-[3-pyridinylmethyl]ester (13). Potassium bicarbonate (12.3 g, 0.123 mol) was added to thiobenzoic acid (14.2 g, 0.097) in 200 mL ethanol in a 500 mL RBF, and the slurry was swirled with gentle heating until $CO_2$ effervescence ceased. 3-(chloromethyl)pyridine hydrochloride (10.2 g, 0.060 mol) was added next, and the RBF was placed in an oil bath to stir at 50° C. for 2.5 hrs. The reaction mixture was poured into a 1 L separatory funnel containing 10 g potassium carbonate ($K_2CO_3$, 0.072 mol) in 250 mL water, extracted with 150 mL DCM, and the organic phase was washed twice with 250 mL water, gravity filtered, and evaporated to dryness under reduced pressure. The crude product was purified further by washing in 50 mL hot hexane to give, after removal of leftover solvent under reduced pressure, 13 as a brown solid in ca. 96% purity (11.4 g, 0.050 mol, 80% yield). $^1$H NMR: δ=8.64 (d, 1 aromatic H ortho to $CH_2$ at the second C of the pyridine ring, J=1.8 Hz), 8.50 (dd, 1 aromatic H para to $CH_2$ at the sixth C of the pyridine ring, J=4.8, 1.5 Hz), 7.99-7.90 (m, 2 aromatic H ortho to COS), 7.71 (ddd, 1 aromatic H ortho to $CH_2$ at the fourth C of the pyridine ring, J=7.8, 1.8, 1.5 Hz), 7.58 (tt, 1 aromatic H para to COS, J=7.5, 1.2 Hz), 7.49-7.39 (m, 2 aromatic H meta to COS), 7.24 (dd, 1 aromatic H meta to $CH_2$ at the fifth C of the pyridine ring, J=7.8, 4.8 Hz), 4.29 (s, $CH_2$).

1,2-Polybutadiene Functionalization using 9-[2-[(Triphenylmethyl)thio]ethyl]carbazole (14)

Synthesis of 9-(2-Chloroethyl)carbazole (7). The procedure was outlined in the description of the preparation of 8. $^1$H NMR (300 MHz, $CDCl_3$): δ=8.09 (d, 2 carbazole H, J=7.8 Hz), 7.50-7.37 (m, 4 carbazole H), 7.29-7.20 (m, 2 carbazole H), 4.60 (t, $NCH_2$, J=7.2 Hz), 3.83 (t, $CH_2Cl$, J=7.2 Hz). $^{13}$C NMR (300 MHz, $CDCl_3$): δ=140.07, 125.91, 123.07, 120.50, 119.50, 108.43, 44.64, 40.99.

Synthesis of 9-[2-[(Triphenylmethyl)thio]ethyl]carbazole (14). Potassium carbonate (4.4 g, 32 mmol), triphenylmethyl mercaptan (Alfa Aesar, 98%, 3.1 g, 11 mmol), and 9-(2-chloroethyl)carbazole (2.1 g, 9.1 mmol) were stirred at r.t. in 50 mL DMF for 5 hrs, after which the reaction mixture was transferred to a 500 mL separatory funnel containing 100 mL water and extracted with 50 mL chloroform. The organic layer was washed twice with 100 mL water, the solvent was evaporated under reduced pressure, and the crude product was purified by washing 3 times in 75 mL hot ethanol.

Filtration of the solids and removal of remaining solvent under reduced pressure gave analytically pure 14 as ultrafine, white needles (3.1 g, 6.6 mmol, 72% yield). $^1$H NMR (300 MHz, $CDCl_3$): δ=8.03 (d, 2 carbazole H, J=7.8 Hz), 7.43-7.14 (m, 4 carbazole H and 15 phenyl H), 7.00 (d, 2 carbazole H, J=8.1 Hz), 4.06 (t, $NCH_2$, J=8.1 Hz), 2.75 (t, $SCH_2$, J=8.1 Hz). $^{13}$C NMR (300 MHz, $CDCl_3$): δ=144.61, 139.76, 129.69, 128.01, 126.86, 125.56, 122.79, 120.27, 119.00, 108.54, 67.39, 42.37, 30.22.

Functionalization Procedure and Results. To compound 14 (0.25 g, 0.5 mmol) dissolved in 10 mL chloroform in a 100 mL Schlenk tube were added triethylsilane (Alfa Aesar, 98%, 0.08 g, 0.7 mmol) and trifluoroacetic acid (TFA, 0.5 mL, 5% vol), and the mixture was stirred 1-2 hrs at r.t. After addition of 1,2-PB (0.2 g, 4 mmol vinyl groups, dissolved in 10 mL chloroform) and AIBN (0.03 g, 0.2 mmol), the contents of the Schlenk tube were degassed in 3 freeze-pump-thaw cycles, then allowed to react at 55° C. for 3 hrs. Following reaction, the polymer solution was transferred to a 100 mL jar containing a small amount of BHT, concentrated by evaporation of all but the last 10 mL solvent under an argon stream, and precipitated in cold methanol. Final purification of the polymer was achieved by reprecipitation from a DCM solution with cold methanol, (2-3 times), followed by drying to constant weight under vacuum at r.t. Reaction conditions and results for a specific example are given in Table A.1 (first entry).

1,2-Polybutadiene Functionalization Using Thiobenzoic acid S-[3-(9-carbazolyl)propyl]ester (16)

Synthesis of 9-Allylcarbazole (15). Carbazole (10.1 g, 0.057 mol) and potassium hydroxide (88% wt pellets, crushed, 7.1 g, 0.11 mol) were stirred in 100 mL DMSO at 50° C. for 30 min before dropwise addition of allyl bromide (14.7 g, 0.118 mol). After 15 min the reaction mixture was poured into a 500 mL separatory funnel containing 100 mL chloroform and washed 5 times with 200 mL water to give, after solvent evaporation at 60° C. under reduced pressure, compound 15 in >99% purity as a dark brown, viscous syrup which solidified upon cooling (11.9 g, 0.057 mol, 100% yield). $^1$H NMR (300 MHz, $CDCl_3$): δ=8.14-8.06 (m, 2 carbazole H), 7.49-7.32 (m, 4 carbazole H), 7.28-7.19 (m, 2 carbazole H), 6.04-5.90 (m, CH=$CH_2$), 5.19-5.10 (m, Z-HCH=CH), 5.07-4.97 (m, E-HCH=CH), 4.92-4.85 (m, $NCH_2$). $^{13}$C NMR (300 MHz, $CDCl_3$): δ=140.34, 132.27, 125.67, 122.90, 120.33, 119.00, 116.74, 108.74, 45.21.

Synthesis of Thiobenzoic acid S-[3-(9-carbazolyl)propyl] ester (16). Thiobenzoic acid (30 g, 0.20 mol) was added to 9-allylcarbazole (11.9 g, 0.057 mol) in 100 mL toluene, and the reaction was carried out at 90° C. with argon purge via radical mechanism using AIBN as the initiator (1.8 g, 11 mmol, in 300 mg increments at 1 hr intervals). After 6 hrs the reaction mixture was poured into a 1 L separatory funnel containing 20 g sodium bicarbonate ($NaHCO_3$, 0.24 mol) in 250 mL water, extracted with 100 mL chloroform, and the organic phase was washed twice with 200 mL water before solvent removal under reduced pressure. The crude product was subsequently washed in 100 mL hot hexane, 150 mL ethanol, and finally 150 mL of 15:1 ethanol:chloroform. Evaporation of leftover solvent at 80° C. under reduced pressure yielded compound 16 in ca. 90% purity as a dark brown, viscous syrup which solidified upon cooling (9.35 g, 0.024 mol, 42% yield, ~10% wt dibenzoyl disulfide). $^1$H NMR (300 MHz, $CDCl_3$): δ=8.10 (d, 2 carbazole H, J=8.1 Hz), 8.00-7.95 (m, 2 aromatic H ortho to COS), 7.62-7.41 (m, 3 aromatic H meta and para to COS plus 4 carbazole H), 7.27-7.19 (m, 2 carbazole H), 4.43 (t, $NCH_2$, J=6.9 Hz), 3.06 (t, $SCH_2$, J=6.9 Hz), 2.26 (tt, $NCH_2CH_2CH_2S$, J=6.9, 6.9 Hz). $^{13}$C NMR (300 MHz, $CDCl_3$): δ=191.56, 140.25, 136.88, 133.50, 128.65, 127.23, 125.75, 122.91, 120.41, 119.00, 108.55, 41.65, 28.95, 26.41.

Functionalization Procedure and Results. Reaction conditions and results for a specific example are given in Table A.1 (second entry).

TABLE A1

Reaction Conditions and Results for 1,2-PB Functionalization Using Compounds 14 and 16

| Entry[a] | [PB] (g/mL) | [Thiol][b] | [AIBN] (g/mL) | Rxn time (hrs) | $X_{funct}$[c] % | $M_W$[d] (kg/mol) | PDI[d] | New H NMR peaks above 2.2 ppm for modified PB (all peaks are broad) |
|---|---|---|---|---|---|---|---|---|
| 820kPB14 | 0.011 | 0.1 | 0.002 | 2.9 | 6 | 945 | 2.08 | 8.12-8.04 (2H), 7.52-7.39 (4H), 7.27-7.19 (2H), 4.56-4.43 (2H), 2.97-2.83 (2H) |

TABLE A1-continued

Reaction Conditions and Results for 1,2-PB Functionalization Using Compounds 14 and 16

| Entry[a] | [PB] (g/mL) | [Thiol][b] | [AIBN] (g/mL) | Rxn time (hrs) | $X_{funct}$[c] % | $M_W$[d] (kg/mol) | PDI[d] | New H NMR peaks above 2.2 ppm for modified PB (all peaks are broad) |
|---|---|---|---|---|---|---|---|---|
| 92kPB16 | 0.003 | 1.1 | 0.003 | 3.0 | 19 | 187 | 1.34 | 8.15-8.03 (2H), 7.56.-7.37 (4H), 7.28-7.15 (2H), 4.50-4.27(2H), 2.62-2.30 (4H) |

[a]Modified PB polymers were named so that the prefix corresponds to the molecular weight of the starting 1,2-PB chain, and the suffix represents the reagent used.
[b]In molar equivalents of 1,2-PB monomer units.
[c]The fracton of reacted 1,2-PB units that bear functional groups (refer to text).
[d]Measurements as described in Experimental section using the Waters setup (the 1,2-PB prepolymers had PDI values of 1.07 and 1.26 for the 92 kg/mol and 820 kg/mol chains, respectively).

General Procedure for 1,2-PB Functionalization Using a Protected Thiol PhCOSR (Scheme 1). To the thioester PhCOSR (1-4 mmol) dissolved in 25-75 mL DMF in a 250 mL RBF were added hydrazine monohydrochloride (ca. 4 equiv., 4-16 mmol) and sodium acetate (ca. 8 equiv., 8-32 mmol). The RBF was purged with argon for ca. 10 min and left to stir at r.t. for 2-4 hrs, resulting in 95-100% cleavage of the thioester (verified by NMR analysis). The thio product was extracted into 30-40 mL chloroform after addition of 100 mL water; the organic phase was washed 4 times with 150 mL water, and transferred into a 100 mL Schlenk tube containing 1,2-PB (0.1-0.2 g, 2-4 mmol, dissolved in 10 mL chloroform) and AIBN (50-250 mg, 0.3-1.5 mmol). The contents of the Schlenk tube were degassed in 3 freeze-pump-thaw cycles, and then allowed to react at 55° C. for 2-6 hrs. Following reaction, the polymer solution was transferred to a 100 mL jar containing a small amount of 2,6-ditert-butyl-4-methylphenol (BHT), concentrated by evaporation of all but the last 10 mL solvent under an argon stream, and precipitated with cold methanol. Final purification of the polymer was achieved by reprecipitation from a DCM or THF solution (containing ca. 1% wt BHT) with cold methanol (repeated 2-4 times), followed by drying to constant weight under vacuum at r.t.

General Procedure for 1,2-PB Functionalization Using an Acyl Chloride RCOCl (Scheme 3). To 1,2-PB (0.1-0.5 g, 2-9 mmol) dissolved in 15-30 mL THF in a 100 mL Schlenk tube was added a 10 mL THF solution of 2-mercaptoethanol (BME, 0.5-2 equiv., 1-20 mmol) and AIBN (15-50 mg, 0.1-0.3 mmol). The contents of the Schlenk tube were degassed in 3 freeze-pump-thaw cycles, and then allowed to react at 55° C. for 2-3 hrs. Following reaction, the polymer solution was transferred to a 100 mL jar containing a small amount of BHT and precipitated in cold methanol. The polymer was purified by reprecipitation from a THF solution (containing ca. 1% wt BHT) with cold methanol (repeated 1-2 times), followed by drying to constant weight under vacuum at r.t. To the 2-hydroxyethylthio-functionalized 1,2-PB polymer (0.1-0.5 g) dissolved in 10-25 mL DCM in a 100 mL RBF were added triethylamine ($Et_3N$, 3-5 mol. equiv. of functionalized monomer units) and the acyl chloride RCOCl (2.5-3 mol. equiv. of functionalized monomer units), and the reaction mixture was stirred 3-4 hrs at r.t. Following reaction, the polymer solution was transferred to a 100 or 250 mL jar containing a small amount of BHT, washed with 50-100 mL water and again with 50-100 mL aqueous sodium bicarbonate (discarding the wash each time), concentrated by evaporation of all but the last 10 mL DCM under an argon stream, and finally precipitated with cold methanol. Final purification of the polymer was achieved by reprecipitation from a DCM solution (containing ca. 1% wt BHT) with cold methanol (repeated 2-3 times), followed by drying to constant weight under vacuum at r.t.

Alkylation of Nucleophiles to Introduce Primary Halide or Alcohol Moieties. To generate ω-chloroalkyl or ω-bromoalkyl derivatives, alkylation of nucleophiles is usually done using α,ωdibromo- or dichloro-alkanes, e.g., reaction of 4'-hydroxy-biphenyl-4-carbonitrile with 1,6-dibromohexane[25] or carbazole with 1,2-dichloroethane[26]. Unfortunately, when using these reagents bisubstitution is always an issue. In addition, in the case of very basic nucleophiles (e.g. deprotonated carbazole), elimination competes effectively; hence, yields tend to be low and product purification usually requires column chromatography. Yields of >50% were not achieved for the synthesis of 7 according to published methods[26] using $KOH/K_2CO_3$ as base in 1,2 dichloroethane with tetrabutylammonium bromide as phase-transfer catalyst. Chloroethylation of nucleophiles with 2-chloroethyl-p-toluenesulfonate (1) in DMSO at low to moderate temperatures overcame both problems stated above. First, the use of p-toluenesulfonate (tosylate) as leaving group and of a polar aprotic solvent both favor substitution over elimination[27]; second, because tosylate is a significantly better leaving group than chlorine, quantitative conversion of both carbazole and 4'-hydroxy-biphenyl-4-carbonitrile to the chloroethyl derivatives (compounds 7, 2) was achieved without measurable formation of side-products. Excess 1 could be reacted quantitatively to 1,2-dichloroethane with KCl in a few hours, so that product in quantitative yields and >95% purity could be obtained by mere liquid-liquid extraction and removal of solvent and dichloroethane at reduced pressure.

Alkylation of nucleophiles to generate co-hydroxyalkyl derivatives is usually done using ω-bromo-1-alkanols or ω-chloro-1-alkanols with $K_2CO_3$ or NaH as base in DMF, acetone, or ethanol as solvent (for instance, alkylation of 4'-hydroxy-biphenyl-4-carbonitrile with bromodecanol[28] or chlorohexanol[29]). Published yields for such reactions are usually <85%, and column chromatography is typically necessary for isolation of the product. Here it was discovered that alkylation of 4'-hydroxy-biphenyl-4-carbonitrile with commercially available $H(OCH_2CH_2)_nCl$ (n=1-3, inexpensively available from Wako Chemicals) in DMSO with $K_3PO_4$ as base gave quantitative conversion, and that product (compound 4 or analog) in >99% purity could be obtained by mere washes due to the good water solubility of the chloride reagent.

$^{13}C$ NMR Resonances of Select Compounds

All $^{13}C$ NMR spectra were obtained using a Varian Mercury 300 spectrometer (corresponding to 74.5 MHz for $^{13}C$), recorded in $CDCl_3$, and referenced to tetramethylsilane. Information compiled in the Spectral Database for Organic Compounds (available online at http://riodb01.ibase.aist.go.jp/sdbs/cgi-bin/direct_frame top.cgi) was used in the process of assigning $^{13}C$ NMR resonances.

2-Chloroethyl-p-toluenesulfonate (1). $^{13}$C NMR: δ=145.30 (e), 132.44 (b), 130.00 and 127.97 (c and d), 69.02 (f, 40.83 (g), 21.67 (a).

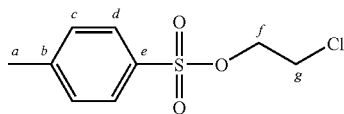

4'-(2-(Benzoylthio)ethoxy)[1,1'-biphenyl]-4-carbonitrile (3). $^{13}$C NMR: δ=191.40 (e), 159.00 (j), 145.11 (n), 136.64 (d), 133.69 (a), 132.57 (p), 131.89 (m), 128.70 and 127.30 (b and c), 128.43 (l), 127.13 (o), 119.09 (r), 115.21 (k), 110.14 (q), 66.70 (g), 28.13 (f).

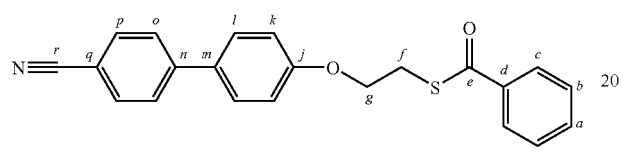

4'-(2-(2-(Benzoylthio)ethoxy)ethoxy) [1,1'-biphenyl]-4-carbonitrile (6). $^{13}$C NMR: δ=191.54 (e), 159.35 (j), 145.12 (n), 136.82 (d), 133.48 (a), 132.54 (p), 131.63 (m), 128.61 and 127.23 (b and c), 128.30 (l), 127.07 (O), 119.10 (r), 115.22 (k), 110.06, (q), 70.05 and 69.38 (h and i), 67.50 (g), 28.65 (f).

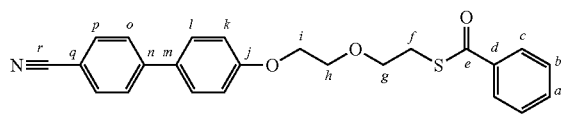

Thiobenzoic acid S-[2-(9-carbazolyl)ethyl]ester (8). $^{13}$C NMR: δ=191.73 (e), 140.07 (h), 136.71 (d), 133.73 (a), 128.74 and 127.35 (b and c), 125.91 (j), 122.98 (m), 120.40 (l), 119.26 (k), 108.74 (i), 42.42 (g), 27.28 (f).

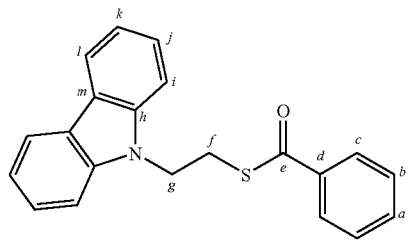

3,5-Dinitrobenzoic acid 3-(acetylthio)propyl ester (10). $^{13}$C NMR: δ=195.36 (b), 162.49 (f), 148.67 (i), 133.81 (g), 129.52 (h), 122.47 (j), 65.21 (e), 30.64 (a), 28.68 and 25.50 (c and d).

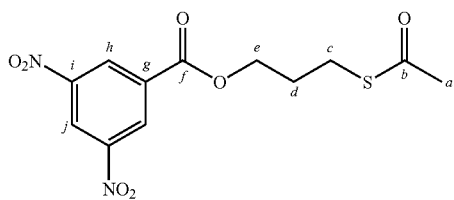

4-Hydroxybenzoic acid 2-(benzoylthio)ethyl ester (12). $^{13}$C NMR: δ=191.42 (e), 166.27 (h), 160.24 (l), 136.65 (d), 133.68 (a), 132.09 (j), 128.70 and 127.32 (b and c), 122.13 (i), 115.28 (k), 63.11 (g), 27.86 (f.

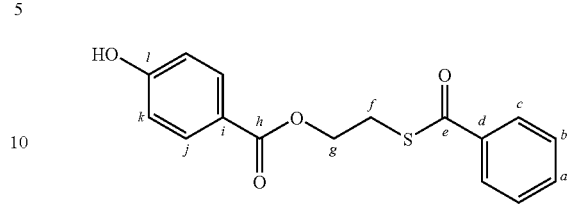

Thiobenzoic acid S-[3-pyridinylmethyl]ester (13). $^{13}$C NMR: δ=190.74 (e), 150.14 (h), 148.62 (i), 136.48 and 136.42 (d and k), 133.70 and 133.65 (a and g), 128.71 and 127.31 (b and c), 123.46 (j), 30.38 (f).

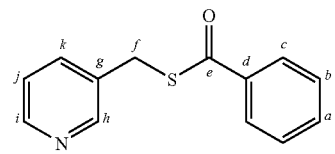

$^1$H NMR Spectra of Select Functionalized Polymers

All spectra were taken in CDCl$_3$, resulting in a solvent peak in each case at δ=7.24 ppm. Peaks near 1.6 ppm correspond to water, and visible peaks at δ=6.97, 2.27, and 1.43 ppm belong to BHT. Representative Spectra are shown in FIGS. 1-6.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

When a group of substituents is disclosed herein, it is understood that all individual members of those groups and all subgroups, including any isomers and enantiomers of the group members, and classes of compounds that can be formed using the substituents are disclosed separately. When a Markush group or other grouping is used herein, all individual members of the group and all combinations and sub-combinations possible of the group are intended to be individually included in the disclosure. When a compound is described herein such that a particular isomer or enantiomer of the compound is not specified, for example, in a formula or in a chemical name, that description is intended to include each isomer and enantiomer of the compound described individually or in any combination. When an atom is described herein, including in a composition, any isotope of such atom is intended to be included. Specific names of compounds are intended to be exemplary, as it is known that one of ordinary skill in the art can name the same compounds differently. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure.

All patents and publications mentioned in the specification are indicative of the levels of skill of those skilled in the art to which the invention pertains. References cited herein are incorporated by reference herein in their entirety to indicate the state of the art, in some cases as of their filing date, and it is intended that this information can be employed herein, if needed, to exclude (for example, to disclaim) specific embodiments that are in the prior art. For example, when a compound is claimed, it should be understood that compounds known in the prior art, including certain compounds disclosed in the references disclosed herein (particularly in referenced patent documents), are not intended to be included in the claim.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example or illustration and not of limitation.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. Antonietti, M.; Forster, S.; Hartmann, J.; Oestreich, S. Macromolecules 1996, 29, (11), 3800-3806.
2. Kramer, E.; Forster, S.; Goltner, C.; Antonietti, M. Langmuir 1998, 14, (8), 2027-2031.

3. Kukula, H.; Schlaad, H.; Antonietti, M.; Forster, S. Journal of the American Chemical Society 2002, 124, (8), 1658-1663.
4. Forster, S.; Antonietti, M. Advanced Materials 1998, 10, (3), 195-217.
5. Pollino, J. M.; Stubbs, L. P.; Weck, M. Journal of the American Chemical Society 2004, 126, (2), 563-567.
6. Carlise, J. R.; Weck, M. Journal of Polymer Science Part a-Polymer Chemistry 2004, 42, (12), 2973-2984.
7. Meyers, A.; Weck, M. Macromolecules 2003, 36, (6), 1766-1768.
8. Kimyonok, A.; Weck, M. Macromolecular Rapid Communications 2007, 28, (2), 152-157.
9. South, C. R.; Burd, C.; Weck, M. Accounts of Chemical Research 2007, 40, (1), 63-74.
10. Schulz, D. N.; Turner, S. R.; Golub, M. A. Rubber Chemistry and Technology 1982, 55, (3), 809-859.
11. Chung, T. C.; Raate, M.; Berluche, E.; Schulz, D. N. Macromolecules 1988, 21, (7), 1903-1907.
12. Ramakrishnan, S. Macromolecules 1991, 24, (13), 3753-3759.
13. Kempe, M. D. Rheology and Dynamics of Side-Group Liquid Crystalline Polymers in Nematic Solvents. Ph.D. Thesis, California Institute of Technology, Pasadena, Calif., 2003.
14. Guo, X. Y.; Farwaha, R.; Rempel, G. L. Macromolecules 1990, 23, (24), 5047-5054.
15. Ameduri, B.; Boutevin, B.; Nouiri, M. Journal of Polymer Science Part a-Polymer Chemistry 1993, 31, (8), 2069-2080.
16. Boutevin, G.; Ameduri, B.; Boutevin, B.; Joubert, J. P. Journal of Applied Polymer Science 2000, 75, (13), 1655-1666.
17. Schapman, F.; Couvercelle, J. P.; Bunel, C. Polymer 1998, 39, (20), 4955-4962.
18. Justynska, J.; Hordyjewicz, Z.; Schlaad, H. Polymer 2005, 46, (26), 12057-12064.
19. Justynska, J.; Hordyjewicz, Z.; Schlaad, H. Macromolecular Symposia 2006, 240, 41-46.
20. Geng, Y.; Discher, D. E.; Justynska, J.; Schlaad, H. Angewandte Chemie-International Edition 2006, 45, (45), 7578-7581.
21. Hordyjewicz-Baran, Z.; You, L. C.; Smarsly, B.; Sigel, R.; Schlaad, H. Macromolecules 2007, 40, (11), 3901-3903.
22. Ren, Y.; Lodge, T. P.; Hillmyer, M. A. Macromolecules 2001, 34, (14), 4780-4787.
23. Scruggs, N. R. Coupling Polymer Thermodynamics and Viscoelasticity to Liquid Crystalline Order Self-Assembly and Relaxation Dynamics of Block Copolymers in a nematic Solvent. Ph.D. Thesis, California Institute of Technology, Pasadena, Calif., 2007.
24. Verduzco, R. Self-Assembled Liquid Crystal Polymer Gels. Ph.D. Thesis, California Institute of Technology, Pasadena, Calif., 2007.
25. Yamaguchi, A.; Maeda, Y.; Yokoyama, H.; Yoshizawa, A. Chem. Mater. 2006, 18, (24), 5704-5710.
26. Bogdal, D.; Yashchuk, V.; Pielichowski, J.; Ogul'Chansky, T.; Warzala, M.; Kudrya, V. Journal of Applied Polymer Science 2002, 84, (9), 1650-1656.
27. Smith, M. B.; March, J., March's Advanced Organic Chemistry. Reactions, Mechanisms, and Structure. 5th ed.; John Wiley & Sons, Inc: 2001.
28. Nakatsuji, S.; Ikemoto, H.; Akutsu, H.; Yamada, J. i.; Mori, A. J. Org. Chem. 2003, 68, (5), 1708-1714.
29. Bhatt, J. J. Journal of organometallic chemistry 1991, 413, (1-3), 263.
30. Brace, N, O. Journal of Organic Chemistry 1966, 31, (9), 2879-2885.
31. Patai, S., The Chemistry of the Thiol Group, Part 1. Wiley: 1974; ch 4.
32. Kocienski, P. J., Protecting Groups. 3rd ed.; Thieme: 2004; ch 5.
33. Fabris, L.; Antonello, S.; Armelao, L.; Donkers, R. L.; Polo, F.; Toniolo, C.; Maran, F. J. Am. Chem. Soc. 2006, 128, (1), 326-336.
34. Moreau, X.; Campagne, J. M. Journal of Organic Chemistry 2003, 68, (25), 9874-9874.
35. Narayan, R. S.; VanNieuwenhze, M. S. Organic Letters 2005, 7, (13), 2655-2658.
36. Oila, M. J.; Tois, J. E.; Koskinen, A. M. P. Tetrahedron Letters 2005, 46, (6), 967-969.
37. Wuts, P. G. M., Greene's Protective Groups in Organic Synthesis/Peter G. M. Wuts and Theodora W. Greene. 4th ed.; Wiley-Interscience: 2007; ch 6.
38. Hinou, H.; Sun, X. L.; Ito, Y. J. Org. Chem. 2003, 68, (14), 5602-5613.
39. Morii, Y.; Matsuda, H.; Ohara, K.; Hashimoto, M.; Miyairi, K.; Okuno, T. Bioorganic & Medicinal Chemistry 2005, 13, (17), 5113-5144.
40. Rich, J. R.; Wakarchuk, W. W.; Bundle, D. R. Chemistry-a European Journal 2006, 12, (3), 845-858.
41. Cramer, N. B.; Scott, J. P.; Bowman, C. N. Macromolecules 2002, 35, (14), 5361-5365.
David, R. L. A. and Kornfield, Julia A., Macromolecules 2008, 41, (4), 1151-1161.
Neises, B. and Steglich, W., Angew. Chem. Int. Ed. Engl., 1978, 17, (7), 522-524.
Pittelkow, M., Kamounah, F. S., Boas, U., Pedersen, B., Christensen, J. B., Synthesis, 2004, 15, 2485-2492.
U.S. Pat. Nos. 2,947,731; 3,705,882; 3,882,156; 4,565,854; 6,977,292; 7,301,045.
U.S. Patent Publication Nos. 2005/0014903; 2007/0021554; 2008/0070786.
PCT International Publication Nos. WO 2004/060863; WO 2007/028612.
Mukoyama Mitsuaki et al., Japanese Publication No. 05286894A

We claim:
1. A method of making a functionalized polymer using a thiol-ene reaction comprising:
providing a functionalized thioester having the following formula:

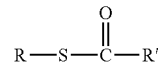

wherein R is a functional group and COR' is a protecting group;
cleaving the functionalized thioester, forming a functional thiol and an acyl group;
providing a polymer having a pendant vinyl group;
reacting the polymer with the functional thiol whereby a functionalized polymer is formed, wherein the functional thiol is not isolated prior to reacting with the polymer.
2. The method of claim 1, wherein the cleaving step is performed by reacting the functionalized thioester with a cleaving agent.
3. The method of claim 2, wherein the cleaving agent is a hydrazine salt or solution thereof.

4. The method of claim 1, wherein the protecting group is an acetyl or benzoyl group.

5. The method of claim 1, wherein the polymer is selected from the group consisting of: a polymer or copolymer of butadiene, isoprene, 2-n-heptyl-1,3-butadiene, ethylene, isobutylene, 1-butene, acrylonitrile, methacrylonitrile, crotonitrile, vinyl acetate, vinyl benzoate, vinyl methyl ether, vinyl n-butyl ether, allyl propionate, allyl benzoate, allyl methyl ester, styrene, vinyl benzyl chloride, divinylbenzene, butadiene, or 5-vinyl-2-norbornene.

6. The method of claim 5, wherein the polymer comprises a 1,2 polybutadiene unit.

7. The method of claim 1, wherein the functional group is selected from the group consisting of: amino acid, peptide, polypeptide, nucleic acid, lipid, carbohydrate, carbazole, benzoate, phenol, pyridine, cyanobiphenyl, perfluorocarbon, polyethylene oxide and polypropyleneoxide groups.

* * * * *